US007147839B2

(12) United States Patent
Sampath et al.

(10) Patent No.: US 7,147,839 B2
(45) Date of Patent: Dec. 12, 2006

(54) METHODS FOR EVALUATING TISSUE MORPHOGENESIS AND ACTIVITY

(75) Inventors: Kuber T. Sampath, Holliston, MA (US); Charles M. Cohen, Weston, MA (US)

(73) Assignee: Curis, Inc., Cambridge, MA (US)

( * ) Notice: Subject to any disclaimer, the term of this patent is extended or adjusted under 35 U.S.C. 154(b) by 0 days.

(21) Appl. No.: 09/423,943

(22) PCT Filed: May 29, 1998

(86) PCT No.: PCT/US98/10909

§ 371 (c)(1), (2), (4) Date: Mar. 8, 2000

(87) PCT Pub. No.: WO98/54572

PCT Pub. Date: Dec. 3, 1998

(65) Prior Publication Data

US 2003/0109686 A1 Jun. 12, 2003

(51) Int. Cl.
*A61K 49/00* (2006.01)
*A61P 19/08* (2006.01)

(52) U.S. Cl. .......................................... 424/9.2; 514/12

(58) Field of Classification Search .................. 514/12, 514/2; 435/1.1, 7.21

See application file for complete search history.

(56) References Cited

U.S. PATENT DOCUMENTS

| | | | |
|---|---|---|---|
| 4,968,590 A | 11/1990 | Kuberasampath et al. | |
| 5,011,691 A | 4/1991 | Oppermann et al. | |
| 5,013,649 A | 5/1991 | Wang et al. | |
| 5,169,837 A | 12/1992 | Lagarde et al. | |
| 5,266,683 A | 11/1993 | Oppermann et al. | |
| 5,585,237 A | 12/1996 | Oppermann et al. | |
| 5,641,743 A | 6/1997 | Bohlen et al. | |
| 5,652,118 A | 7/1997 | Ozkaynak et al. | |
| 5,656,593 A | 8/1997 | Kuberasampath et al. | |
| 5,849,686 A | 12/1998 | Kuberasampath et al. | |
| 5,928,940 A | 7/1999 | Sampath et al. | |
| 5,972,884 A | 10/1999 | Cohen et al. | |
| 6,022,853 A | 2/2000 | Kuberasampath et al. | |
| 6,077,823 A | 6/2000 | Kuberasampath et al. | |
| 6,096,706 A * | 8/2000 | Toback et al. | 514/2 |

FOREIGN PATENT DOCUMENTS

| | | |
|---|---|---|
| EP | 0714665 A | 6/1996 |
| EP | 0723031 A | 7/1996 |
| EP | 1 364 655 A1 | 11/2003 |
| WO | WO 88/00205 | 1/1988 |
| WO | WO 90/11366 | 10/1990 |
| WO | WO 91/18098 | 11/1991 |
| WO | WO 92/00382 | 1/1992 |
| WO | WO 92/15323 | 9/1992 |
| WO | WO 93/00432 | 1/1993 |
| WO | WO 93/04692 | 3/1993 |
| WO | WO 93/05172 | 3/1993 |
| WO | WO 93/05751 | 4/1993 |
| WO | WO 93/16099 | 8/1993 |
| WO | WO 94/03200 * | 2/1994 |
| WO | WO 94/03600 | 2/1994 |
| WO | WO 94/06399 | 3/1994 |
| WO | WO 94/06420 | 3/1994 |
| WO | WO 94/06449 | 3/1994 |
| WO | WO 94/10203 | 5/1994 |
| WO | WO 94/15949 | 7/1994 |

(Continued)

OTHER PUBLICATIONS

Kumar et al., American J. Physiology, 1994, vol. 266, pp. F829-F832.*

(Continued)

*Primary Examiner*—David S Romeo
*Assistant Examiner*—Daniel C Gamett
(74) *Attorney, Agent, or Firm*—Fish & Neave IP Group, Ropes & Gray, LLP

(57) ABSTRACT

The present invention is based on the discovery that a true tissue morphogen such as OP-1 provided systemically, alone in its mature dimeric form, or as part of a soluble complex, can induce new replacement tissue regeneration at a localized, permissive defect site distal to the site of administration. Specifically, systemically administered protein is sufficient to induce formation of new functional replacement tissue, sufficient to repair a local defect in a tissue, including skeletal or orthopedic tissues, liver, pancreas, lung, cardiac, renal, uterine, intestinal, gastrointestinal tissue. (As used herein, "orthopedic" or "skeletal" or "joint" or "chondrogenic" tissue is understood to encompass the skeletal and skeletal joint tissues: bone, cartilage, tendon, ligament, and synovial membrane tissues.) It further has been discovered that a single injection of morphogenic protein is sufficient to induce the desired biological effect, and that administration is not time-sensitive, provided mesenchymal progenitor cells are accessible to the defect site. That is, morphogenic protein can be provided to an individual having a local permissive defect site, shortly after creation of the defect, or at some significant time later, including, without limitation, after the initiation of fibrotic tissue formation. Thus, means now are available for enhancing restoration of tissue function and/or repair or regeneration of functional replacement tissue by systemically administering morphogenic protein, at times significantly after creation of the defect. The methods and formulations can be used to repair local defects without requiring surgical intervention; can enhance the rate and quality of new replacement tissue formation, particularly in compromised individuals with a reduced capacity to undergo spontaneous healing, and can be used to induce new tissue formation even after the initiation of fibrosis at the defect site. This discovery is disclosed in copending U.S. Patent Application filed on even date herewith, the disclosure of which is incorporated herein by reference.

22 Claims, 5 Drawing Sheets

FOREIGN PATENT DOCUMENTS

| | | | |
|---|---|---|---|
| WO | WO 94/15965 | | 7/1994 |
| WO | WO 94/15966 | | 7/1994 |
| WO | WO 94/21681 | | 9/1994 |
| WO | WO 94/26892 | | 11/1994 |
| WO | WO 94/26893 | | 11/1994 |
| WO | WO 95/01801 | | 1/1995 |
| WO | WO 95/05846 | * | 3/1995 |
| WO | WO 95/10539 | | 4/1995 |
| WO | WO 95/10635 | | 4/1995 |
| WO | WO 95/10802 | | 4/1995 |
| WO | WO 95/14104 | | 5/1995 |
| WO | WO 95/33830 | | 12/1995 |
| WO | WO 96/01316 | | 1/1996 |
| WO | WO 96/01845 | | 1/1996 |
| WO | WO 96/14335 | | 5/1996 |
| WO | WO 96/30038 | | 10/1996 |
| WO | WO 96/36710 | | 11/1996 |
| WO | WO 96/40297 | | 12/1996 |
| WO | WO 97/32033 | | 9/1997 |
| WO | WO 98/13509 | | 4/1998 |

OTHER PUBLICATIONS

Benet, L, and Sheiner, L., in Goodman and Gilman's The Pharmacological Basis of Therapeutics, 1980, 6th Edition, pp. 1675-1737.*

Basler, K. et al. Control of Cell Pattern in the Neural Tube: Regulation of Cell Differentiation by dorsalin-1, a Novel TGFβ Family Member. *Cell* 73, 687-702 (May 21, 1993).

Bock, L. C. et al. Selection of single-stranded DNA molecules that bind and inhibit human thrombin. *Nature* 355, 564-566 (Feb. 6, 1992).

Celeste, A. J. et al. Identification of transforming growth factor β family members present in bone-inductive protein purified from bovine bone. *PNAS* 87, 9843-9847 (Dec. 1990).

Famulok, M. & Szostak, J. W. In Vitro Selection of Specific Ligan-binding Nucleic Acids. *Angew. Chem. Int. Ed. Engl.* 31, 979-988 (1992).

Hogan, B. L. M. Bone Morphogenentic proteins: multifunctional regulators of vertebrate development. *Genes & Development* 10, 1580-1594 (1996).

Jones, W. K. et al. Osteogenic Protein-1 (OP-1) Expression and Processing in Chinese Hamster Ovary Cells: Isolation of a Soluble Complex Containing the Mature and Pro-Domains of OP-1. *Growth Factors* 11, 215-225 (1994).

Lee, Se-Jin. Expression of growth / differentiation factor 1 in the nervous system: Conservation of a bicistronic structure. *PNAS* 88, 4250-4254 (May 1991).

Lyons, K. et al. Vgr-1, a mammalian gene related to Xenopus Vg-1, is a member of the transforming growth factor β gene superfamily. *PNAS* 86, 4554-4558 (Jun. 1989).

Massague, J. The Transforming Growth Factor-β Family. *Annu. Rev. Cell Biol.* 6, 597-641 (1990).

Mathiowitz, E. et al. Biologically erodable microspheres as potential oral drug delivery systems. *Nature* 386, 410-414 (Mar. 27, 1997).

Ozkaynak, E. et al. Osteogenic Protein-2. *J. Biol. Chem.* 267, 25220-25227 (1992).

Ozkaynak, E. et al. OP-1 cDNA encodes an osteogenic protein in the TGF-β family. *EMBO J.* 9, 2085-2093 (1990).

Padgett, R. W. et al. A transcript from a Drosophila pattern gene predicts a protein homologous to the transforming growth factor-β family. *Nature* 325, 81-84 (Jan. 1987).

Sampath, T.K. & Reddi, A. H. Homology of bone-inductive proteins from human, monkey, bovine, and rat extracellular matrix. *PNAS* 80, 6591-6595 (Nov. 1983).

Sampath, T. K. et al. Bovine Osteogenic Protein is Composed of Dimers of OP-1 and BMP-2A, Two Members of the Transforming Growth Factor-β Superfamily. *J. Biol. Chem.* 265, 13198-13205 (Aug. 5, 1990).

Storm, E. E. et al. Limb alterations in brachypodism mice due to mutations in a new member of the TGFβ-superfamily. *Nature* 368, 639-643 (Apr. 14, 1994).

Takao, M. et al. Identification of Rat Bone Morphogenetic Protein-3b (BMP-3b), a New Member of BMP-3. *Biochem. Biophys. Res. Comm.* 219, 656-662 (1996).

Tuerk, C.& Gold, L. Systematic Evolution of Ligands by Exponential Enrichment: RNA Ligands to Bacteriophage T4 DNA Polymerase. *Science* 249, 505-510 (Aug. 3, 1990).

Vukicevic, S. et al. Localization of Osteogenic Protein-1 (Bone Morphogenetic Protein-7) During Human Embryonic Development: High Affinity Binding to Basement Membranes. *Biochem. Biophys. Res. Comm.* 198, 693-700 (Jan. 28, 1994).

Weeks, D. L. & Melton, D. A. A Maternal mRNA Localized to the Vegetal Hemisphere in Xenopus Eggs Codes for a Growth Factor Related to TGF-β. *Cell* 51, 861-867 (Dec. 4, 1987).

Wharton, K. A. et al. Drosophila 60A gene, another transforming growth factor β family member, is closely related to human bone morphogenetic proteins. *PNAS* 88, 9214-9218 (Oct. 1991).

Wozney, J. M. et al. Novel Regulators of Bone Formation: Molecular Clones and Activities. *Science* 242, 1528-1534 (Dec. 16, 1988).

Guo, X. et al., Osteogenic protein-1 and related bone morphogenetic proteins regulate dendritic growth and the expression of microtubule-associated protein-2 in rat sympathetic neurons, Neuroscience Letters 245 (1998) pp. 131-134.

* cited by examiner

FIG. 4

% Sequence Similarity to Human OP-1 7-Cysteine Domain

| Sequence | % Similarity | % Non Conservative |
|---|---|---|
| hOP-1 | 100 | 0 |
| mOP-1 | 100 | 0 |
| hOP-2 | 97 | 3 |
| mOP-2 | 97 | 3 |
| BMP-5 | 97 | 3 |
| BMP-6 | 96 | 4 |
| Vgr-1(PT) | 94 | 6 |
| OP-3 | 91 | 9 |
| 60A | 90 | 10 |
| BMP-4 | 90 | 10 |
| BMP-2 | 89 | 11 |
| dpp | 87 | 13 |
| UNIVIN | 87 | 13 |
| dpp(PT) | 86 | 14 |
| Vg-1 | 86 | 14 |
| CDMP-1 | 85 | 15 |
| CDMP-3 | 83 | 17 |
| GDF-3 | 83 | 17 |
| CDMP-2 | 82 | 18 |
| DORSALIN | 79 | 21 |
| GDF-1(PT) | 78 | 22 |
| GDF-10 | 78 | 22 |
| BMP-3b | 78 | 22 |
| BMP-10 | 78 | 23 |
| BMP-3 | 78 | 23 |
| SCREW | 77 | 23 |
| ADMP | 77 | 24 |
| TGF-β2 | 73 | 27 |
| GDF-1 | 73 | 28 |
| BMP-9 | 73 | 28 |
| NODAL | 71 | 29 |
| InhibinβA | 71 | 29 |
| BMP-15 | 71 | 29 |

METHODS FOR EVALUATING TISSUE MORPHOGENESIS AND ACTIVITY

CROSS REFERENCE TO RELATED APPLICATIONS

This application is a national stage filing under 35 U.S.C. 371 of International Application PCT/US/98/10909, filed May 29, 1998, which is a continuation of U.S. application Ser. No. 08/866,827, now abandoned, which claims the benefit of U.S. Provisional Application Nos. 60/048,062 and 60/048,063, filed May 30, 1997, the specifications of each of which are incorporated by reference herein in its entirety.

FIELD OF THE INVENTION

The invention disclosed herein relates to materials and methods for inducing tissue-specific morphogenesis, and methods for evaluating the activity of morphogenic compounds.

BACKGROUND OF THE INVENTION

A class of proteins now has been identified that is competent to act as true tissue morphogens. That is, these proteins are able, on their own, to induce the migration, proliferation and differentiation of progenitor cells into functional replacement tissue. This class of proteins, referred to herein as "osteogenic proteins" or "morphogenic proteins" or "morphogens," includes members of the family of bone morphogenetic proteins (BMPs) identified by their ability to induce ectopic, endochondral bone morphogenesis. The morphogenic proteins generally are classified in the art as a subgroup of the TGF-β superfamily of growth factors (Hogan (1996) *Genes* & Development 10:1580–1594). Members of the morphogen family of proteins include the mammalian osteogenic protein-1 (OP-1, also known as BMP-7, and the *Drosophila* homolog 60A), osteogenic protein-2 (OP-2, also known as BMP-8), osteogenic protein-3 (OP-3), BMP-2 (also known as BMP-2A or CBMP-2A, and the *Drosophila* homolog DPP), BMP-3, BMP-4 (also known as BMP-2B or CBMP-2B), BMP-5, BMP-6 and its murine homolog Vgr-1, BMP-9, BMP-10, BMP-11, BMP-12, GDF3 (also known as Vgr2), GDF8, GDF9, GDF10, GDF11, GDF12, BMP-13, BMP-14, BMP-15, GDF-5 (also known as CDMP-1 or MP52), GDF-6 (also known as CDMP-2), GDF-7 (also known as CDMP-3), the *Xenopus* homolog Vg1 and NODAL, UNIVIN, SCREW, ADMP, and NEURAL.

Members of this family encode secreted polypeptide chains sharing common structural features, including processing from a precursor "pro-form" to yield a mature polypeptide chain competent to dimerize and containing a carboxy terminal active domain, of approximately 97–106 amino acids. All members share a conserved pattern of cysteines in this domain and the active form of these proteins can be either a disulfide-bonded homodimer of a single family member or a heterodimer of two different members (see, e.g., Massague (1990) *Annu. Rev. Cell Biol.* 6:597; Sampath, et al. (1990) *J. Biol. Chem.* 265:13198). See also, U.S. Pat. Nos. 5,011,691; 5,266,683, Ozkaynak et al. (1990) *EMBO J.* 9:2085–2093, Wharton et al. (1991) *PNAS* 88:9214–9218), (Ozkaynak (1992) *J. Biol. Chem.* 267:25220–25227 and U.S. Pat. No. 5,266,683); (Celeste et al. (1991) *PNAS* 87:9843–9847); (Lyons et al. (1989 ) *PNAS* 86:4554–4558). These disclosures describe the amino acid and DNA sequences, as well as the chemical and physical characteristics, of these osteogenic proteins. See also, Wozney et al. (1988) *Science* 242:1528–1534); BMP 9 (WO93/00432, published Jan. 7, 1993); DPP (Padgett et al. (1987) *Nature* 325:81–84; and Vg-1 (Weeks (1987) *Cell* 51:861–867).

The morphogenic activities of these proteins allow them to initiate and maintain the developmental cascade of tissue morphogenesis in an appropriate, morphogenically permissive environment, stimulating stem cells to proliferate and differentiate in a tissue-specific manner, and inducing the progression of events that culminate in new tissue formation. These morphogenic activities also allow the proteins to stimulate the "redifferentiation" of cells previously induced to stray from their differentiation path. The proteins are useful in the replacement of diseased or damaged tissue in a mammal, particularly when the damaged tissue interferes with normal tissue or organ function, such as, for example, damaged lung tissue resulting from emphysema; cirrhotic kidney or liver tissues; damaged heart or blood vessel tissue, as may result from cardiomyopathies and/or atherothrombotic or cardioembolic strokes; damaged stomach tissue resulting from ulceric perforations or their repair; damaged neural tissue as may result form physical injury, degenerative diseases such as Alzheimer's disease or multiple sclerosis or strokes; damaged dentin and periodontal tissues as may result from disease or mechanical injury.

The proteins have been shown to have utility in repairing a number of non-chondrogenic tissues, including dentin, liver, kidney, neural, cardiac lung, gastrointestinal tract tissue and the like. See, for example, W902/15323, published Sep. 17, 1992; W093/04692, published Mar. 18, 1993; W094/06399, published Mar. 31, 1994; W094/03200, published Feb. 17, 1994; W094/06449, published Mar. 31, 1993; W094/06420, published Mar. 31, 1994. See also, U.S. Ser. Nos. 08/404,113; 08/445,467; 08/432,883; 08/155,343; 08/260675; 08/445,468; 08/461,397; 08/480,528; 08/402,542; 08/396,930; 08/751,227; the disclosures of which are incorporated by reference.

Needs remain for compositions and methods for improved means for evaluating the in vivo activity and/or efficacy of these morphogenic proteins and analogs thereof. It is anticipated that different morphogens will have differing specific activities for effecting morphogenesis in a given tissue or organ. It further is anticipated that analogs of morphogens, including candidate non-protein-based "small molecule" functional mimetics, will need to be evaluated for their ability to functionally substitute for a given morphogen in vivo. It further is anticipated that, for a given indication, such as treating an embolic stroke, for example, dosing and routes of administration can vary depending on the individual's overall health, age and condition. Thus, needs also remain for evaluating the pharmacokinetics of a morphogenic protein or analog thereof, including evaluating dosing, preferred administration times, and preferred administration routes for administering a given morphogen, and/or analog to a given individual, for different therapeutic applications.

Accordingly, it is an object of the instant invention to provide formulations and methods of use thereof for quickly evaluating the in vivo activity of morphogens and/or analogs thereof.

These and other objects, along with advantages and features of the invention disclosed herein, will be apparent from the description, drawings and claims that follow.

SUMMARY OF THE INVENTION

The present invention is based on the discovery that a true tissue morphogen such as OP-1 provided systemically, alone in its mature dimeric form, or as part of a soluble complex, can induce new replacement tissue regeneration at a localized, permissive defect site distal to the site of administration. Specifically, systemically administered protein is sufficient to induce formation of new functional replacement tissue, sufficient to repair a local defect in a tissue, including skeletal or orthopedic tissues, liver, pancreas, lung, cardiac, renal, uterine, intestinal, gastrointestinal tissue. (As used herein, "orthopedic" or "skeletal" or "joint" or "chondrogenic" tissue is understood to encompass the skeletal and skeletal joint tissues: bone, cartilage, tendon, ligament, and synovial membrane tissues.) It further has been discovered that a single injection of morphogenic protein is sufficient to induce the desired biological effect, and that administration is not time-sensitive, provided mesenchymal progenitor cells are accessible to the defect site. That is, morphogenic protein can be provided to an individual having a local permissive defect site, shortly after creation of the defect, or at some significant time later, including, without limitation, after the initiation of fibrotic tissue formation. Thus, means now are available for enhancing restoration of tissue function and/or repair or regeneration of functional replacement tissue by systemically administering morphogenic protein, at times significantly after creation of the defect. The methods and formulations can be used to repair local defects without requiring surgical intervention; can enhance the rate and quality of new replacement tissue formation, particularly in compromised individuals with a reduced capacity to undergo spontaneous healing, and can be used to induce new tissue formation even after the initiation of fibrosis at the defect site. This discovery is disclosed in copending U.S. Patent Application filed on even date herewith, the disclosure of which is incorporated herein by reference.

As disclosed herein, a method now is provided for effectively evaluating the in vivo activity of a given morphogen or morphogen analog in repairing a local tissue defect. The method comprises providing the morphogen or analog, as the case may be, systemically to an animal afflicted with a local tissue defect in need of repair. The morphogen or analog can be provided by any systemic means, including orally, intravenously or intraperitoneally. The tissue can be any tissue in need of repair, including without limitation, any of the tissues described herein. In addition, the methods provided herein allow one to evaluate readily preferred formation compositions, including the value, if any, of added molecules such as targeting agents, antibiotics, analgesics, and the like; and to evaluate preferred binding agents, solutions, and other components adding value as administration route excipients.

The methods allow one to rapidly test any morphogen, including any naturally-occurring or biosynthetic, e.g., genetically engineered variant thereof, including chimeras and muteins.

The methods also allows one to evaluate optional dosing strategies, administration routes and/or administration times for a given morphogen, morphogen analog, therapeutic indication and/or individual condition. It is anticipated that these strategies will vary to some degree based on the type of defect, the type of tissue, the choice of morphogen, and/or analog, and the condition of the individual. For example, aged individuals, or individuals having reduced blood flow, may require different dosing strategies and/or administration routes as compared with younger individuals in good health.

Testing dosing strategies in these different patient populations allows one to determine optimal molecules and conditions for administration.

The method provided herein also provides a reliable in vivo means for evaluating the efficacy of a candidate morphogen analog determined to have utility in functionally mimicking a morphogen, as determined by one or more in vitro assays. In vitro assays for evaluating morphogen or morphogen analog activity are described in numerous public sources, including WO 93/05751, published Apr. 1, 1993, as well as in U.S. Ser. No. 08/432,883, filed May 2, 1995, and U.S. Ser. No. 08/727,118, filed Oct. 8, 1996, the disclosures of which are incorporated herein by reference. The methods also provide ready and reliable means for determining what, if any, may be the toxicity level of a given candidate analog.

The assay involves creating a local defect in a tissue of interest and administering the morphogen or analog systemically. In one embodiment, a biocompatible, biodegradable matrix is implanted at a subcutaneous site and the morphogen or analog is administered systemically, for example, interperitoneally on intravenously. In one embodiment, the matrix is a bone-derived collagen matrix and active morphogens or analogs are competent to induce new cartilage and bone formation at the collagen implant site, which can be evaluated by standard histology 12 days post implant. In another embodiment, a permissive local defect site is created in existing tissue.

As contemplated herein, a "permissive" site is a local site of a tissue defect in need of repair and to which progenitor cells are accessible. Mesenchymal progenitor cells typically become available to a defect locus at least by 6–24 hours post trauma as part of the inflammatory response triggered by the initial trauma. Specifically, these progenitor cells (stem cells) are recruited to the site by the chemokines and growth factors activated by the inflammatory response. These recruited progenitor cells form a condensed mass at the defect locus, typically referred to as a callus, and are available to differentiate into a specific tissue type in response to locally available, specific, tissue-inductive signals. In the absence of such tissue-inductive signals, these progenitor cells typically are induced to differentiate into fibroblasts by the chemokines and growth factors (e.g., PDGF, TGF$\beta$, IL-1 and the like). The committed fibroblasts then are competent to generate a non-specific extracellular matrix characteristic of fibrotic "scarring" tissue and which can be resorbed over time. Such scarring is characteristic of cirrhotic tissue or tissue infarcts, as can occur in lung, liver, kidney, and cardiac tissues, for example.

In another embodiment, a local defect site is created in a tissue of interest, such as lung, cardiac, pancreas, liver, gastrointestinal tract, and neural tissue, for example. The methods and compositions are contemplated to assist in evaluating preferred administration protocols for repairing and/or restoring function to tissues such as skeletal tissues (including bone, cartilage, ligament, tendon and synovial membrane tissues), and liver, kidney, lung, pancreas, spleen, uterine, cardiac, thyroid, gastrointestinal tract, neural tissues, sense organs, and the like.

In one preferred embodiment, the assay can be used to evaluate optimal administration times. For example, in one embodiment, the protein or candidate analog is provided at least 6 hours post trauma, or 10–24 hours post trauma. In another embodiment, protein or analog is provided systemically any time between 24–36 hrs and/or between 36–72 hrs, and/or between 72–120 hrs, and/or between 120–168 hrs post-trauma. In another embodiment, the assay is used to evaluate optimal administration routes, times, and dosages for promoting or inducing tissue repair under refractory healing conditions. As used herein, "refractory healing" refers to any defect where, due to the nature of the defect or the condition of the individual (aged, obese, smoker, diabetic, steroidal user), for example, spontaneous formation of new replacement tissue sufficient to correct the defect does not occur.

In another aspect, the instant invention provides methods for assessing the ability of a morphogen or morphogen analog to regenerate lost or damaged tissue in vivo in an existing tissue or organ. In another aspect, the invention provides methods for assessing the ability or a morphogen or analog to maintain normal tissue function following tissue injury, or in anticipation of such injury. As disclosed herein, methods of repair include treatment of both closed and open defects. Examples of defects include, but are not limited to, tissue defects.

In another aspect, the instant invention provides a kit for practice of the above-described methods. As contemplated herein, one embodiment of a kit includes a collagen matrix implant material and a formulation of morphogen and/or analog for systemic administration. In another embodiment, the kit comprises the morphogenic protein or analog and systemic administration carrier (e.g., a liquid carrier) are packaged in the same receptacle. In other embodiments, the morphogenic protein or analog is provided in lyophilized form and reconstituted in a given carrier, e.g., aqueous buffer, in the same receptacle.

Exemplary formulations for testing using the methods of the invention include providing the protein or analog as a liquid formulation administered intravenously. In another embodiment, the protein or analog is provided in a liquid formulation intraperitoneally. In still another embodiment, the protein or analog is provided in liquid or tablet or other non-liquid form for oral administration, including disposed in biocompatible, biodegradable or bioerodible microspheres and other delivery vehicles, or otherwise combined with suitable binding agents as described herein. Another preferred embodiment can have a dry powder configuration that is solubilized just prior to administration. One suitable formulation results from first dispersing morphogenic protein or analog in a liquid carrier such as water with or without excipient, followed by lyophilization. In one formulation tested, the composition is a solution made by combining the protein together with an acidic buffered solution, e.g., pH 4.0–4.5, for example an acetate or citrate buffer. Still another formulation is a suspension formed by disbursing osteogenic protein in a physiologically buffered solution, such as phosphate buffered saline (PBS).

As contemplated herein, morphogenic proteins useful for evaluating in the methods of the invention include, but are not limited to, OP-1, OP-2, BMP-2, BMP-4, BMP-5 and BMP-6. A currently preferred morphogenic protein is OP-1. As used herein, the terms "morphogen", "bone morphogen", "bone morphogenic protein", "BMP", "osteogenic protein" and "osteogenic factor" embrace the class of proteins typified by human osteogenic protein 1 (hOP-1). Nucleotide and amino acid sequences for hOP-1 are provided in Seq. ID Nos. 1 and 2, respectively. For ease of description, hOP-1 is recited herein below as a representative morphogenic protein. It will be appreciated by the artisan of ordinary skill in the art, however, that OP-1 merely is representative of the TGF-β subclass of true tissue morphogens, and is not intended to limit the description. Other known, and useful proteins include, BMP-2, BMP-3, BMP-3b, BMP-4, BMP-5, BMP-6, BMP-8, BMP-9, BMP-10, BMP-11, BMP-12, BMP-13, BMP-15, GDF-1, GDF-2, GDF-3, GDF-5, GDF-6, GDF-7, GDF-8, GDF-9, GDF-10, GDF-11, GDF-12, NODAL, UNIVIN, SCREW, ADMP, NEURAL and morphogenically active amino acid variants thereof. In one preferred embodiment, the proteins useful in the invention include biologically active species variants of any of these proteins, including conservative amino acid sequence variants, proteins encoded by degenerate nucleotide sequence variants, and osteogenically active proteins sharing the conserved seven cysteine skeleton as defined herein and encoded by a DNA sequence competent to hybridize to a DNA sequence encoding a morphogenic protein disclosed herein, including, without limitation, OP-1, BMP-5, BMP-6, BMP-2, BMP-4 or GDF-5, GDF-6 or GDF-7. In another embodiment, useful proteins include those sharing the conserved seven cysteine domain and sharing at least 70% amino acid sequence homology (similarity) within the C-terminal active domain, as defined herein. In another embodiment, useful proteins include those sharing greater than 60% identity in the C-terminal domain. In still another embodiment, useful osteogenic proteins can be defined as osteogenically active proteins having any one of the generic sequences defined herein, including OPX (SEQ ID No: 3) and Generic Sequences 7 and 8 (Seq. ID Nos. 4 and 5), or Generic Sequences 9 and 10 (Seq. ID Nos. 6 and 7).

As contemplated herein, the methods of the invention are useful for evaluating morphogenic properties of a morphogen analog, e.g., any candidate compound competent to induce a morphogen-mediated biological effect. Morphogen analogs include homologs and ligand analogs that can substitute for a morphogen in a ligand-morphogen receptor binding intraction, as well as functional mimetics competent to induce biological effect of morphogenesis by inducing a downstream effect normally stimulated by ligand-morphogen receptor binding under native conditions.

As a result of the present analog identification methods, the invention provides means for identifying and producing therapeutic-grade morphogen analogs. The invention further provides for identifying and producing a derivative of a candidate morphogen analog in which any undesirable properties of the initially identified analog, such as in vivo toxicity or a tendency to degrade upon storage, are mitigated.

Still another embodiment contemplates assay methods useful in determining proper morphogen or analog dosing and/or progression of morphogenesis.

In any treatment method of the invention, "administration of morphogenic protein or analog" refers to the administration of the protein or an analog thereof, either alone or in combination with other molecules. For example, the mature form of the morphogen may be provided in association with its precursor "pro" domain, which is known to enhance the solubility of the protein. As used herein, "soluble form" of a morphogenic protein is understood to mean the dimeric species complexed with part or all of a morphogenic protein pro domain. See, for example, WO94/03600, published 18 Feb. 1994 and/or Jones et al., (1994) *Growth Factors* 11: 215–225, for a detailed description of the soluble complex form of morphogenic proteins. Other useful molecules known to enhance protein solubility include casein and other milk components, as well as various serum proteins.

The foregoing and other objects, features and advantages of the present invention will be made more apparent from the following detailed description of the invention.

DESCRIPTION OF THE DRAWINGS

FIG. 4 is a table showing the percent homology of various morphogens to human OP-1 c-terminal 7-cysteine region.

DETAILED DESCRIPTION

Figure 1:
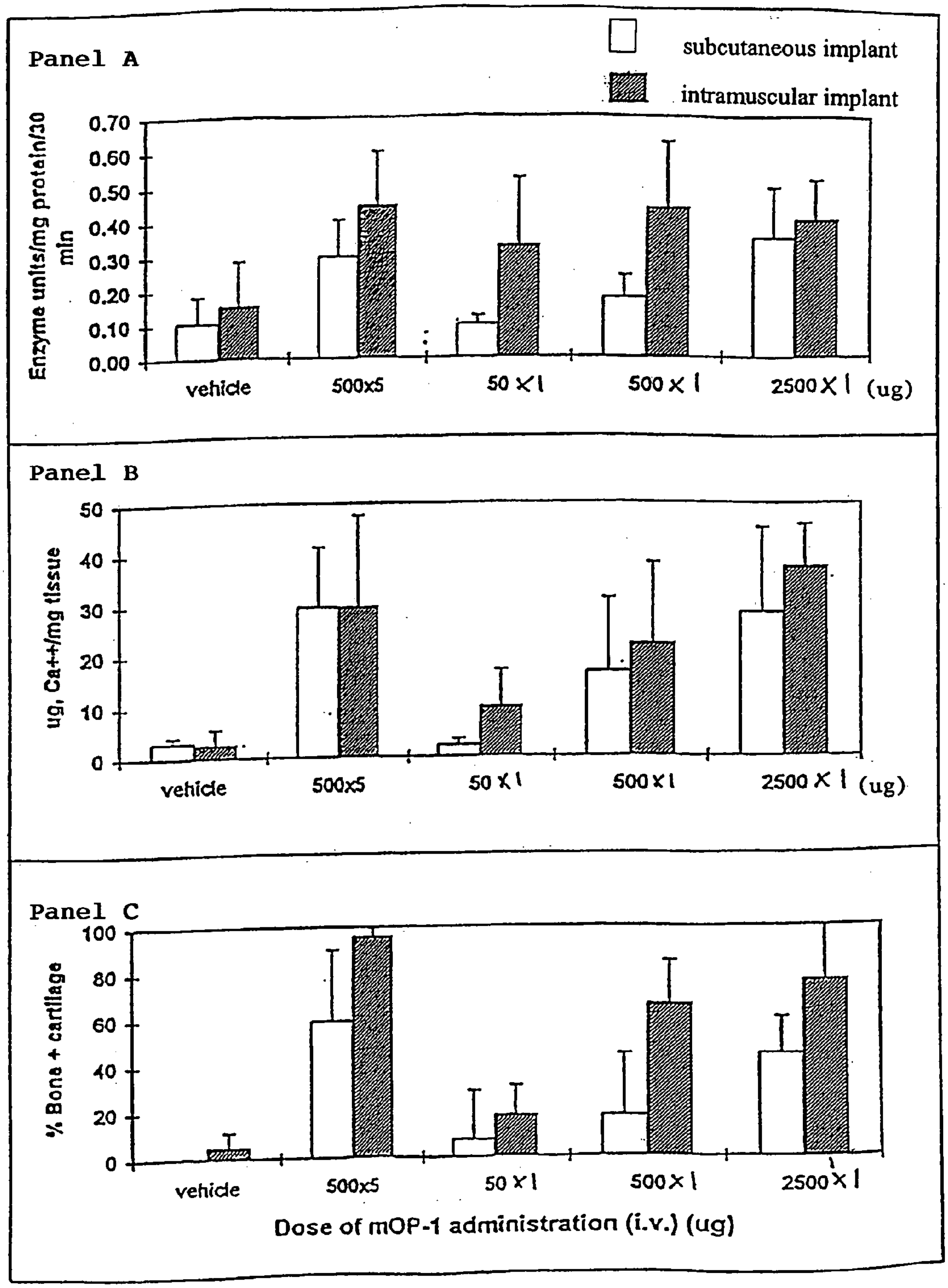
FIGS. 1A–1C is a graph showing bone forming activity induced by systemic OP-1 administration. Bovine collagen carrier (25 mg) was implanted at subcutaneous sites (open bar) and intramuscular sites (filled bar). OP-1 was administered via the tail vein (500 ug×5 times, 50 ug×1,500 ug×1, or 2500 ug×1). Panel 1A shows the amount of alkaline phosphatase induced. Panel 1B shows the calcium content of the implant, and Panel 1C shows the histologic examination of the implants harvested at 12 days after implantation. See Example 4 for experimental details.

An assay method now has been discovered for evaluating the efficacy and/or pharmacokinetic properties of morphogenic proteins and analogs thereof. The method comprises the steps of systemically administering a morphogenic protein or an analog thereof in an animal having a local permissive defect site and evaluating the ability of the protein or analog administered, under the conditions of the assay, to induce formation of functional replacement tissue at the defect site. The method does not require inclusion of an exogenous matrix material or the need to provide the protein or analog directly to the defect locus. A local permissive defect site readily can be created by implanting a matrix material in a intramuscular or subcutaneous site in an animal, such as a rat. In one embodiment, the material is a demineralized, deproteinated collagen matrix. In another embodiment, the matrix is any other biocompatable, biodegradable, biologically inert scaffolding material, preferably porous and substantially acellular. In still another embodiment, a permissive local defect site is created in an existing tissue. For example, a fracture can be induced in bone, and a tear or chondral defect can be induced in cartilage. Similar mechanical or toxin-induced defects can be induced in lung, cardiac, liver, pancreatic, uterine and other tissues, to name but a few.

The defects also can be created in standard, well characterized animal models representative of different patient populations, as a means for evaluating morphogen or analog efficacy and/or pharmacokinetics in different therapeutic conditions. Examplary patient populations include, without limitation, juveniles, aged, diabetic, hypertensive, obese, immune-comprised animals, and the like.

Provided below are detailed descriptions of suitable morphogenic proteins and analogs, and formulations useful in the methods, compositions and assays of this invention, as well as methods for their administration and application; and numerous, nonlimiting examples which 1) illustrate the suitability of the morphogenic proteins, analogs, formulations, methods and assays described herein; and 2) provide assays with which to test candidate proteins and analogs, formulations for their efficacy in different tissues, for repairing various defects, and for measuring efficacy and/or pharmacokinetics in different patient populations.

In order to more clearly and concisely describe the subject matter of the claimed invention, the following definitions are intended to provide guidance as to the meaning of specific terms used in the written description and appended claims.

As embodied herein, the expression "maintaining normal tissue function" means both regaining or restoring tissue function lost due to an injury or acquired or congenital defect, as well as protecting the tissue at risk of damage from injury. Restoring tissue function can include regenerating new tissue and/or simulating existing differentiated tissue cells to continue expressing their phenotype as in the case of senescent cells. "Depressed tissue function" level refers to a diminished to deficient tissue function as a result of a tissue injury or disease. The expression "enhance viability of" a tissue or organ, as used herein, means protection from, reduction of and/or elimination of reduced or lost tissue or organ function as a result of tissue necrosis and/or fibrosis, particularly immune response-mediated tissue necrosis and/or fibrosis. "Alleviating" means protection from, reduction of and/or elimination of, undesired tissue destruction. "Transplanted" living tissue includes both tissue grafts and cellular transplants, as in the case of transplanted isolated progenitor or stem cells, for example, which may be implanted alone or in association with a temporary scaffolding. Tissues may be autologous or allogenic tissue and/or synthetic tissue created, for example, by culturing hepatic cells in the presence of an artificial matrix. "Morphogenically permissive environment" is understood to mean an environment competent to allow tissue morphogenesis to occur. Finally, "symptom alleviating cofactor" refers to one or more pharmaceuticals which may be administered together with the therapeutic agents of this invention and which alleviate or mitigate one or more of the symptoms typically associated with the tissue injury and/or tissue function loss. Exemplary cofactors include antibiotics, antiseptics, non-steroidal anti-inflammatory agents, and the like.

"Defect" or "defect site" or "defect locus", as contemplated herein, can define any structural disruption in a tissue or organ requiring repair. Systemically administered morphogenic protein can enhance the rate of recruiting, proliferating and differentiating mesenchymal progenitor cells (stem cells). Repair of such tissue defects is dependent on the presence of available or accessible mesenchymal progenitor cells.

"Repair" is intended to mean formation of new tissue which is sufficient to restore function and/or otherwise functionally correct a defect in a mammal. Repair does not, however, mean, or otherwise necessitate, a process of complete healing or a treatment which is 100% effective at restoring a defect to its pre-defect physiological/structural/mechanical state.

In addition to morphogenic proteins, various systemic factors, hormones, enzymes, enzyme inhibitors and/or chemoattractant/chemotactic factors, therapeutic compositions, antibiotics, or other bioactive agents also can be contained within formulation for use in the invention. Thus, various known growth factors such as EGF, PDGF, IGF, FGF, TGF-a, and TGF-β can be combined with a morphogenic formulation described herein and administered systemically.

"Morphogen", "morphogenic protein", "osteogenic protein", or "bone morphogenic protein," generally is understood to mean a protein which can induce the full cascade of morphogenic events culminating in new organ-specified tissue formation. As described elsewhere herein, the class of proteins is typified by human osteogenic protein (hOP1). Other osteogenic proteins useful in the practice of the invention include osteogenically active forms of OP1, OP2, OP3, BMP2, BMP3, BMP4, BMP5, BMP6, BMP9, DPP, Vg1, Vgr, 60A protein, GDF-1, GDF-3, GDF-5, 6, 7, BMP10, BMP11, BMP12, BMP13, BMP15, UNIVIN, NODAL, SCREW, ADMP or NEURAL and amino acid sequence variants thereof. In one currently preferred embodiment, osteogenic protein includes any one of: OP1, OP2, OP3, BMP2, BMP4, BMP5, BMP6, BMP9, and amino acid sequence variants and homologs thereof, including species homologs thereof Particularly preferred proteins are those comprising an amino acid sequence having at least 70% homology with the C-terminal 102–106 amino acids, defining the conserved seven cysteine domain, of human OP-1, BMP2, and related proteins. Certain preferred embodiments of the instant invention comprise the osteogenic protein, OP-1 and proteins sharing greater than 60% amino acid sequence identity with OP-1 in the C-terminal seven cysteine domain. Certain other preferred embodiments comprise mature OP-1 solubilized in a physiological saline solution. As further described elsewhere herein, the proteins suitable for use with Applicants' invention can be identified by means of routine experimentation using the art-recognized bioassay described by Reddi and Sampath. A detailed description of useful morphogenic proteins is provided below.

In general terms, an "analog" is understood to be a functional equivalent of a given substance and can be a substitute for said substance, including as a therapeutic substitute. An analog also can be a structural equivalent. As used herein, a "morphogen analog" is a substance that mimics a biological effect induced and/or mediated by a morphogen, such as OP-1. Any substance having such mimetic properties, regardless of the chemical or biochemical nature thereof, can be used as a morphogen analog herein. A morphogen analog as contemplated herein can be a simple or complex substance produced by a living system or through chemical or biochemical synthetic techniques. It can be a substance that occurs in nature or it can be a novel substance, e.g., prepared according to principles of rational drug design. It can be a substance that structurally resembles a solvent-exposed morphogen surface epitope implicated in receptor interactions, a substance that otherwise stimulates a morphogen receptor displayed on the surface of a morphogen responsive cell, or a cell-membrane permanent substance or otherwise intracellular-acting molecule that interacts with an intracellular component of the signal transduction machinery of a morphogen-responsive cell and thereby stimulates a morphogen specific biological effect. Such intracellular acting morphogen analogs also are referred to herein as "downstream morphogenesis inducers". As used herein, a morphogen analog can be referred to as a "mimic" or a "mimetic".

In another embodiment, the morphogen analog useful in the present invention comprises a candidate compound or an agent which acts as an agonist of a morphogen receptor. An "agonist" of a receptor means a compound which binds to the receptor and for which such binding has a similar functional result as binding of a morphogen to the receptor. That is, the compound upon interaction with the receptor, produces the same or a substantially similar transmembrane and/or intracellular effect as a morphogen. Thus, an agonist of a morphogen receptor binds to the receptor and such binding has the same or a similar functional result as morphogen binding (e.g., induction of morphogenesis). The activity or potency of an agonist can be less than that of the natural morphogen, in which case the agonist is said to be a "partial agonist," or it can be equal to or greater than that of the natural ligand, in which case it is said to be a "full agonist." Thus, for example, a small peptide or other molecule which can mimic the activity of a morphogen in binding to and activating the morphogen's receptor can be employed as an equivalent of the morphogen. Preferably the agonist is a full agonist, but partial morphogen receptor agonists can also be advantageously employed. Methods of identifying such agonists are disclosed herein and include assays for compounds which induce morphogen-mediated responses (e.g., induction of differentiation of metanephric mesenchyme, induction of endochondral bone formation, and the like). Such an agonist also can be referred to as a morphogen "mimic," "mimetic," or "analog."

Also by way of example and without being limited hereto, another type of morphogen analog useful in the present invention can be prepared through judicious application of the principles of biosynthetic antibody binding site (BABS) technology as set forth in U.S. Pat. Nos. 5,132,405, 5,091, 513 and 5,258,498, the teachings of which are incorporated herein by reference. BABS analog constructs can be prepared from antibodies, preferably produced by hybridoma cells, that bind specifically to a morphogen cell surface receptor. Alternatively, BABS analysis can be prepared from anti-idiotypic antibodies specifically reactive with the antigen binding site of an antibody that blocks morphogen biological activity. Vukicevic et al. (1994) *Biochem. Biophys. Res. Comm.* 198:693–700 teaches the preparation of OP-1 specific monoclonal antibodies. Skilled artisans will appreciate that such antibodies can be used as immunogens in the routine preparation of anti-idiotypic antibodies from which BABS analogs of the present invention can be prepared.

A structurally distinct class of morphogen analogs, again set forth herein for illustration and not for limitation, can be prepared through application of the principles of directed molecular evolution as set forth in Tuerk et al. (1990) *Science* 249:505–510, Famulok et al. (1992) *Angew. Chem. Intl. Ed. Engl.* 31:979–988 and Bock et al. (1992) *Nature* 355:564–556, the teachings of each of which are incorporated by reference herein. The directed molecular evolution process involves isolation of a nucleic acid molecule, typically an RNA, that binds with high affinity to a selected ligand such as a protein. Such a nucleic acid molecule is referred to in the art as an "aptamer." The desired aptamer is initially present in a random pool of nucleic acid molecules, and is isolated by performing several rounds of ligand-affinity based chromatography alternating with PCR-based amplification of ligand-binding nucleic acids. Bock et al. (1992), above, have demonstrated the preparations of aptamers, suitable for in vivo use in mammals, that specifically inhibit the blood clot promoting factor, thrombin. As contemplated herein, such aptamers can be derived from a morphogen.

Yet another structurally distinct class of morphogen analogs can be prepared by selecting appropriate members of a random peptide library (Scott et al. (1990) *Science* 249: 386–390) or a combinatorially synthesized random library of organic or inorganic compounds (Needels et al. (1993) *Proc. Natl. Acad. Sci. USA* 90:10700–10704; Ohlmeyer et al. (1993) *Proc. Natl. Acad. Sci. USA* 90:10922–10926). Skilled artisans will appreciate that the foregoing and other related technologies, taken together with long-established principles of screening biologically-produced substances, offer a wide array of candidate substances for screening for morphogen analog activity. As will be appreciated by the skilled artisan, the product of such a library screen can mimic OP-1 or another morphogen as a ligand for morphogen receptor binding. Alternatively, the product can induce a morphogen-specific biological effect through one or more intracellular interactions. Thus, a naturally-sourced or genetically engineered OP-1 or other morphogen analog, morphogen receptor analog or biological functional mimetic, can comprise a polypeptide, polynucleotide, carbohydrate, lipid, amino acid, nucleic acid, sugar, fatty acid, steroid, or a derivative of any one of the aforementioned compounds. It can be an intermediate or end product of metabolism of a eukaryotic or prokaryotic cell. Alternatively, the analog can be a biological response modifier or a toxin. Finally, the analog can be a molecule competent to induce expression of an endogenous morphogen.

"Binding Agent", as used herein, means any physiologically-compatible material which, when admixed with a morphogenic protein as defined herein, enhances a desired physical property of the formulation without substantially destroying the biological activity of the protein in vivo. Binding agents are contemplated to have utility when oral administration is desired. Among the other characteristics of a preferred binding agent is an ability to render the device: pliable, shapeable and/or malleable. Additionally, in certain preferred embodiments, a binding agent can achieve the aforementioned features and benefits when present in low proportions.

Those binding agents contemplated as useful herein include, but are not limited to: art-recognized suspending agents, viscosity-producing agents and emulsifying agents. In particular, art-recognized agents, such as cellulose gum derivatives, sodium alginate, and gelatin powder can be used. More particularly, cellulosic agents such as alkylcelluloses, are preferred including agents such as methylcellulose, methylhydroxyethylcellulose, hydroxyethylcellulose, hydroxypropylmethylcellulose, carboxymethylcellulose, sodium carboxymethylcellulose, and hydroxyalkylcelluloses, to name but a few. Currently, the most preferred is carboxymethylcellulose, including the sodium salt thereof. Other useful binding agents include, but are not limited to, dextran, mannitol, white petrolatum, sesame oil and admixtures thereof. In view of the teachings set forth herein, the artisan can identify suitable equivalents of the above-identified binding agents using merely routine experimentation and ordinary skill.

"Wetting Agent" or "carrier", as used herein, means any physiologically-compatible aqueous solution, provided it does not interfere with the in vivo biological activity of the osteogenic protein. Currently preferred wetting or carrier agents include aqueous solutions competent to solubilize or otherwise suspend the protein in solution such that it can be administered in liquid form to an individual. Currently preferred carriers include, without limitation, physiological saline, phosphate buffered saline (PBS), acetate buffered solutions (pH4.5) and the like. Equivalents can be identified by the artisan using no more than routine experimentation and ordinary skill.

Exemplary Tissues:

Some exemplary tissues and the etiologies of various defects treatable by the methods and compositions described herein and enabled by this disclosure, and useful in the evaluative assays enabled by this disclosure, are listed below. It will be understood by those skilled in the art that the recitation is not intended to be limiting in anyway. In addition to the tissues recited herein, other tissues, including, without limitation, pancreas, uterine, ovarian, gastrointestinal tract, colon, intestinal, dermal, and periodontal tissues are treatable by the methods and compositions described herein.

Cardiac Tissue:

Adult mammalian cardiac muscle has extremely limited powers of growth and regeneration. As a result, damage or loss of myocardium due, for example, to myocardial infarction, congestive heart failure, physical trauma (e.g., in an automobile accident), or infection, typically results in a permanent and often progressive loss of functional myocardium.

Subjects that can benefit from the methods and compositions of the invention include individuals at risk of, or afflicted with, loss of or damage to myocardium. Such subjects include subjects already afflicted with the loss of myocardial tissue, such as those which have already suffered a myocardial infarction, physical trauma to the heart (e.g., in an automobile accident), or those already suffering from congestive heart failure, as well as subjects reasonably expected to suffer from myocardial infarction or congestive heart failure.

The methods and compositions are competent to induce a process of proliferation and/or differentiation of progenitor stem cells at a site of lost or damaged mammalian myocardium to produce new and functional mammalian myocardium, thereby restoring or regenerating the lost or damaged tissue in whole or in part. The treatment also can be used to correct chronically deteriorating mammalian myocardium (e.g., due to congestive heart failure or chronic myopathy). In one embodiment, a subject that has already suffered from one or more myocardial infarcts can undergo surgery to remove scar tissue, and morphogen or analog can be administered systemically to induce cardiac tissue morphogenesis.

Neural Tissue:

Like cardiac tissue, mammalian neural tissue has extremely limited powers of growth and regeneration. The morphogen or analog can be used in the methods and compositions of the present invention upon injury to a neural pathway, or in anticipation of such injury, for a time and at a concentration sufficient to maintain the neural pathway, including repairing damaged pathways, or inhibiting additional damage thereto.

In particular, the morphogens and analogs can be used to repair damaged pathways, including transected or otherwise damaged nerve fibers (nerves) requiring regeneration of neuronal processes, particularly axons, over extended distances to bridge a gap in the nerve itself, or between the nerve and a post-synaptic cell. Specifically, the morphogens and analogs described herein are capable of stimulating complete axonal nerve regeneration, including vascularization and reformation of the protective myelin sheath. They also are competent to form functional replacement neural pathways in the central nervous system, such as in the repair of damaged or detached retinas, or other damage to the optic nerve.

The morphogens and analogs also are useful for enhancing survival of neuronal cells at risk of dying, thereby preventing, limiting or otherwise inhibiting damage to neural pathways. Non-mitotic neurons are at risk of dying as a result of a neuropathy or other cellular dysfunction of a neuron or glial cell inducing cell death, or following a chemical or mechanical lesion to the cell or its surrounding tissue. The chemical lesions may result from known toxic agents, including lead, ethanol, ammonia, formaldehyde and many other organic solvents, as well as the toxins in cigarette smoke and opiates. Excitatory amino acids, such as glutamate also may play a role in the pathogenesis of neuronal cell death (see Freese et al. (1990) *Brain Res.* 521:254–264). Neuronal cell death also is thought to be a significant contributing factor in a number of neurodegenerative diseases, including Alzheimer's disease, Huntington's chorea, and Parkinson's disease, amyotrophic lateral sclerosis and multiple sclerosis. The etiology of these neuropathies may be metabolic, as results in hepatic encephalopathy, infectious, toxic, autoimmune, nutritional or ischemic. In addition, ethanol and a number of other toxins also have been identified as significant contributing factors in neurodegenerative diseases.

The morphogens and analogs described herein also are useful for providing neuroprotective effects to alleviate neural pathway damage associated with the body's immune/inflammatory response to an initial injury to nerve tissue. Such a response may follow trauma to nerve tissue, caused, for example, by an autoimmune dysfunction, neoplastic lesion, infection, chemical or mechanical trauma, disease, by interruption of blood flow to the neurons or glial cells, for example following ischemia or hypoxia, or by other trauma to the nerve or surrounding material. For example, the primary damage resulting from hypoxia or ischemia-reperfusion following occlusion of a neural blood supply, as in an embolic stroke, is believed to be immunologically associated. In addition, at least part of the damage associated with a number of primary brain tumors also appears to be immunologically related. Providing the morphogen to the mammal systemically, for example, intravenously or indirectly by oral administration, may be used to alleviate and/or inhibit the immunologically related response to a neural injury. Where the injury is to be induced, as during surgery or other aggressive clinical treatment, the morphogen or agent may be provided prior to induction of the injury to provide a neuroprotective effect to the nerve tissue at risk.

In still another aspect, the invention described herein provides methods for evaluating the efficacy and/or pharmacokinetics of morphogens and analogs competent to support the growth and maintenance of differentiated neurons, including inducing neurons to continue expressing their phenotype. This activity can be used in the treatment of nerve tissue disorders where loss of function is caused by reduced or lost cellular metabolic function and cells become senescent or quiescent, such as is thought to occur in aging cells and to be manifested in Alzheimer's disease. Providing morphogen systemically by parenteral or oral administration stimulates these cells to continue expressing their phenotype, significantly inhibiting and/or reversing the effects of the cellular metabolic dysfunction, thereby maintaining the neural pathway at risk.

The invention also can be used for evaluating morphogens, analogs and their pharmacokinetics in treating traumatic injuries to the central nervous system that are caused by mechanical forces, such as a blow to the head. Trauma can involve a tissue insult selected from abrasion, incision, contusion, puncture, compression, etc., such as can arise from traumatic contact of a foreign object with any locus of or appurtenant to the mammalian head, neck or vertebral column. Other forms of traumatic injury can arise from constriction or compression of mammalian CNS tissue by an inappropriate accumulation of fluid (e.g., a blockade or dysfunction of normal cerebrospinal fluid or vitreous humor fluid production, turnover or volume regulation, or a subdural or intracranial hematoma or edema). Similarly, traumatic constriction or compression can arise from the presence of a mass of abnormal tissue, such as a metastatic or primary tumor.

Liver:

Unlike most other organs in the body the liver has a defined regenerative capacity following hepatic tissue damage or cell death. Specifically, while hepatocytes do not proliferate actively following fetal and post natal liver growth, normally quiescent hepatocytes do divide in response to cell death or loss of liver tissue. However, where tissue damage is extensive and/or chronic, permanent tissue damage can result, reducing the organ's viability and functional capacity. Permanent hepatic tissue damage typically is characterized by extensive necrosis and/or fibrogenesis or scarring (cirrhosis). Another source of nonreparative damage results from hepatic neoplasms and metastatic carcinomas.

Where either the mass of liver cells is sufficiently diminished or their function sufficiently impaired, hepatic failure ensues. The etiology of hepatic failure may be metabolic (e.g., altered bilirubin metabolism or fatty acid storage), infectious (e.g., induced by viral hepatitis, hepatic schistomiasis, syphilis, or ascariaris), toxic (e.g., induced by ethanol, ammonia, phenol, and other environmental toxins, fatty acids, drugs and/or their metabolites), autoimmune, ischemic or nutritional (e.g., alcoholic liver disease liver failure also is characterized by severe and often life-threatening bleeding, due to the reduced production of essential blood clotting factors). Hepatic failure also can induce neurological dysfunction, characterized broadly as hepatic encephalopathy, as well as associated renal failure, jaundice, pulmonary complications, and a host of disorders associated with hormonal imbalances.

Gastrointestinal Tract

The methods and compositions of the invention are useful for evaluating morphogens and analogs in protecting the luminal lining of the gastrointestinal tract from ulceration, particularly in individuals at risk for ulcer formation. Specifically, the morphogens and analogs described herein can be assessed for their efficacy in limiting the proliferation of epithelial cells, inhibiting the inflammation normally associated with ulcerative disease, inhibiting scar tissue formation, and inducing repair and regeneration of the ulcerated tissue.

In one aspect, the invention features compositions and methods for evaluating optimal therapeutically effective amounts of a morphogenic protein or analog sufficient to maintain the integrity of the GI tract luminal lining that comprise the step of systemically administering to a mammal upon injury to all or a portion of the GI tract luminal lining or in anticipation of such injury and evaluating the repair of the ulcerated tissue, and/or inhibition of damage thereto.

In one preferred embodiment of the invention, the ulcers created for assay and/or treatable according to the invention include those found in the ileum which cause regional ileitis, those found in the colon which cause ulcerative colitis, regional enteritis (Crohn's disease), proctitis and other forms of inflammatory bowel disease (IBD), gastric ulcers such as those found in the stomach, small intestines, duodenum and esophagus; and ulcers found in the mouth. The compositions and methods described herein are particularly useful in treating mucositis lesions caused by chemotherapy or radiation therapy.

Lung:

A variety of lung diseases are characterized by airway inflammation, including chronic bronchitis, emphysema, idiopathic pulmonary fibrosis and asthma. Another type of lung-related inflammation disorders are inflammatory diseases characterized by a generalized, wide-spread, acute inflammatory response such as adult respiratory distress syndrome. Another dysfunction associated with the inflammatory response is that mounted in response to injury caused by hyperoxia, e.g., prolonged exposure to lethally high concentrations of $O_2$ (95–100% $O_2$). Similarly, reduced blood flow to a tissue (and, therefore reduced or lack of oxygen to tissues), as described below, also can induce a primary tissue injury that stimulates the inflammatory response.

The assays of the present invention are competent to evaluate efficacy and/or pharmacokinetics of morphogens and analogs in restoring lung tissue function and/or tissue loss due to these and other sources of lung tissue damage.

The means for making and using the formulations and methods of the invention, as well as other material aspects concerning their nature and utility, including how to make and how to use the subject matter claimed, will be further understood from the following, which constitutes the best mode currently contemplated for practicing the invention. It will be appreciated that the invention is not limited to such exemplary work or to the specific details set forth in these examples.

I. Protein Considerations

A. Biochemical Structural and Functional Properties of Bone Morphogenic Proteins In its mature, native form, natural-sourced morphogenic protein is a glycosylated dimer typically having an apparent molecular weight of about 30–36 kDa as determined by SDS-PAGE. When reduced, the 30 kDa protein gives rise to two glycosylated peptide subunits having apparent molecular weights of about 16 kDa and 18 kDa. In the reduced state, the protein has no detectable osteogenic activity. The unglycosylated protein, which also has osteogenic activity, has an apparent molecular weight of about 27 kDa. When reduced, the 27 kDa protein gives rise to two unglycosylated polypeptide chains, having molecular weights of about 14 kDa to 16 kDa. Typically, the naturally occurring osteogenic proteins are translated as a precursor, having an N-terminal signal peptide sequence typically less than about 30 residues, followed by a "pro" domain that is cleaved to yield the mature C-terminal domain. The signal peptide is cleaved rapidly upon translation, at a cleavage site that can be predicted in a given sequence using the method of Von Heijne (1986) *Nucleic Acids Research* 14:4683–4691. The pro domain typically is about three times larger than the fully processed mature C-terminal domain.

Morphogens comprise a pair of polypeptide chains that, when folded, adopt a configuration sufficient for the resulting dimeric protein to elicit morphogenetic responses in cells and tissue displaying receptors specific for said morphogen. That is, morphogens generally induce all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells. "Progenitor" cells are uncommitted cells that are competent to differentiate into one or more specific types of differentiated cells, depending on their genomic repertoire and the tissue specificity of the permissive environment in which morphogenesis is induced. Morphogens further can delay or mitigate the onset of senescence- or quiescence-associated loss of phenotype and/or tissue function. Morphogens still further can stimulate phenotypic expression of differentiated cells, including expression of metabolic and/or functional, e.g., secretory, properties thereof. In addition, morphogens can induce redifferentiation of committed cells under appropriate environmental conditions. As noted above, a morphogen that induces proliferation and/or differentiation of at least of dentin, cardiac, lung, liver, renal, adrenal, thyroid, ovarian, spleen, neural, pancreas, or gastrointestinal tract tissue, and/or support the growth, maintenance and/or functional properties of any of these tissues, is of particular interest herein.

Morphogenic proteins useful herein include any known naturally-occurring native proteins including allelic, phylogenetic counterpart and other variants thereof, whether naturally-occurring or biosynthetically produced (e.g., including "muteins" or "mutant proteins"), as well as new, biologically active members of the general morphogenic family of proteins.

Particularly useful sequences include those comprising the C-terminal 96 or 102 amino acid sequences of DPP (from *Drosophila*), Vg1 (from *Xenopus*), Vgr-1 (from mouse), the OP1 and OP2 proteins, proteins (see U.S. Pat. No. 5,011,691 and Oppermann et al., as well as the proteins referred to as BMP2, BMP3, BMP4 (see WO88/00205, U.S. Pat. No. 5,013,649 and W091/18098), BMP5 and BMP6 (see WO90/11366, PCT/US90/01630), BMP8 and BMP9. Other proteins useful in the practice of the invention include active forms of OP1, OP2, OP3, BMP2, BMP3, BMP4, BMP5, BMP6, BMP9, GDF-5, GDF-6, GDF-7, DPP, Vg1, Vgr, 60A protein, GDF-1, GDF-3, GDF-5, GDF-6, GDF-7, BMP10, BMP11, BMP13, BMP15, UNIVIN, NODAL, SCREW, ADMP or NURAL and amino acid sequence variants thereof. In one currently preferred embodiment, morphogenic protein include any one of: OP1, OP2, OP3, BMP2, BMP4, BMP5, BMP6, BMP9, and amino acid sequence variants and homologs thereof, including species homologs, thereof.

Publications disclosing these sequences, as well as their chemical and physical properties, include: OP-1 and OP-2: U.S. Pat. Nos. 5,011,691, 5,266,683, Ozkaynak et al. (1990) *EMBO J* 9: 2085–2093; OP-3: WO94/10203 (PCT US93/10520); BMP2, BMP3, BMP4: WO88/00205, Wozney et al. (1988) *Science* 242: 1528–1534); BMP5 and BMP6: Celeste et al. (1991) *PNAS* 87: 9843–9847; Vgr-1: Lyons et al. (1989) *PNAS* 86: 4554–4558; DPP: Padgett et al. (1987) *Nature* 325: 81–84; Vg-1: Weeks (1987) *Cell* 51: 861–867; BMP-9: WO95/33830 (PCT/US95/07084); BMP10: WO94/26893 (PCT/US94/05290); BMP-11: WO94/26892 (PCT/US94/05288); BMP12: WO95/16035 (PCT/US94/14030); BMP-13: WO95/16035 (PCT/US94/14030); GDF-1: WO92/00382 (PCT/US91/04096) and Lee et al. (1991) *PNAS* 88: 4250–4254; GDF-8: WO94/21681 (PCT/US94/03019); GDF-9: WO94/15966 (PCT/US94/00685); GDF-10: WO95/10539 (PCT/US94/11440); GDF-11: WO96/

01845 (PCT/US95/08543); BMP-15: WO96/36710 (PCT/US96/06540); MP121: WO96/01316 (PCT/EP95/02552); GDF-5 (CDMP-1, MP52): WO94/15949 (PCT/US94/00657) and WO96/14335 (PCT/US94/12814) and WO93/16099 (PCT/EP93/00350) and Storm et al., (1994), *Nature* 368:639–643; GDF-6 (CDMP-2, BMP13): WO95/01801 (PCT/US94/07762) and WO96/14335 and WO95/10635 (PCT/US94/14030); GDF-7 (CDMP-3, BMP12): WO95/10802 (PCT/US94/07799) and WO95/10635 (PCT/US94/14030); BMP-3b: Takao, et al., (1996), *Biochem. Biophys. Res. Comm.* 219:656–662; GDF-3: WO94/15965; 60A: Blaster et al., (1993), *Cell* 73:687–702 and GenBank accession number L12032. In another embodiment, useful proteins include biologically active biosynthetic constructs, including novel biosynthetic proteins and chimeric proteins designed using sequences from two or more known osteogenic proteins. See also the biosynthetic constructs disclosed in U.S. Pat. No. 5,011,691, the disclosure of which is incorporated herein by reference (e.g., COP-1, COP-3, COP-4, COP-5, COP-7, and COP-16).

In certain preferred embodiments, morphogenic proteins useful herein include those in which the amino acid sequences comprise a sequence sharing at least 70% amino acid sequence homology or "similarity", and preferably 80% homology or similarity, with a reference morphogenic protein selected from the foregoing naturally occurring proteins. Preferably, the reference protein is human OP-1, and the reference sequence thereof is the C-terminal seven cysteine domain present in morphogenically active forms of human OP-1, residues 330–431 of SEQ ID NO: 2. It will be appreciated that other known morphogenic proteins also can be used as the reference sequence. In one embodiment, a candidate amino acid sequence thought to be functionally equivalent to a reference amino acid sequence can be aligned therewith using the method of Needleman, et al. (1970) *J. Mol. Biol.* 48:443–453, implemented conveniently by computer programs such as the Align program (DNAstar, Inc.). Internal gaps and amino acid insertions in the candidate sequence are ignored for purposes of calculating the defined relationship, conventionally expressed as a level of amino acid sequence homology or identity, between the candidate and reference sequences.

"Amino acid sequence homology" is understood herein to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. Certain particularly preferred morphogenic polypeptide chains share at least 60% amino acid sequence identity with the C terminal seven cysteine domain of the preferred reference sequence of human OP-1, still more preferably at least 65% amino acid sequence identity therewith.

Significant amino acid changes can be made from the reference sequence while retaining morphogenic activity. For example, while the GDF-1 protein sequence shares only about 50% amino acid identity with the hOP-1 sequence described herein, the GDF-1 sequence shares greater than 70% amino acid sequence homology with the hOP-1 sequence, where "homology" is as defined above. Moreover, GDF-1 contains a four amino acid insert (Gly-Gly-Pro-Pro) between the two residues corresponding to residue 372 and 373 of OP-1 (SEQ ID NO: 2). Similarly, BMP-3 has a "extra" residue, a valine, inserted between the two residues corresponding to residues 385 and 386 of hOP-1 (SEQ ID NO: 2). Also, BMP-2 and BMP-4 both are "missing" the amino acid residue corresponding to residue 389 of OP-1 (SEQ ID NO: 2). None of these "deviations" from the reference sequence appear to interfere with biological activity.

As will be understood by those skilled in the art, homologous or functionally equivalent sequences include functionally equivalent arrangements of the cysteine residues within the conserved cysteine skeleton, including amino acid insertions or deletions which alter the linear arrangement of these cysteines, but do not materially impair their relationship in the folded structure of the dimeric protein, including their ability to form such intra- or inter-chain disulfide bonds as may be necessary for biological activity. For example, naturally occurring morphogens have been described in which at least one internal deletion (of one residue; BMP2) or insertion (of four residues; GDF-1) is present but does not abrogate biological activity. Functionally equivalent sequences further include those wherein one or more amino acid residues differ from the corresponding residue of a reference sequence, e.g., the C-terminal seven cysteine domain (also referred to herein as the conserved seven cysteine skeleton) of human OP-1, provided that this difference does not destroy tissue morphogenic activity.

As used herein, "conservative substitutions" are residues that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an accepted point mutation in Dayhoff et al. (1978), 5 *Atlas of Protein Sequence and Structure, Suppl.* 3, ch. 22 (pp. 354–352), Natl. Biomed. Res. Found., Washington, D.C. 20007. Examples of conservative substitutions include the substitution of one amino acid for another with similar characteristics, e.g., substitutions within the following groups are well-known: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. The term "conservative variant" or "conservative variation" also includes the use of a substituted amino acid in place of an unsubstituted parent amino acid in a given polypeptide chain, provided that antibodies having binding specificity for the resulting substituted polypeptide chain also have binding specificity (i.e., "crossreact" or "immunoreact" with) the unsubstituted or parent polypeptide chain.

In other preferred embodiments, the family of morphogenic proteins useful in the present invention, and members thereof, are defined by a generic amino acid sequence. For example, Generic Sequence 7 (SEQ ID NO: 4) and Generic Sequence 8 (SEQ ID NO: 5) disclosed below, accommodate the homologies shared among preferred protein family members identified to date, including at least OP-1, OP-2, OP-3, CBMP-2A, CBMP-2B, BMP-3, 60A, DPP, Vg1, BMP-5, BMP-6, Vgr-1, and GDF-1. The amino acid sequences for these proteins are described herein and/or in the art, as summarized above. The generic sequences include both the amino acid identity shared by these sequences in the C-terminal domain, defined by the six and seven cysteine skeletons (Generic Sequences 7 and 8, respectively), as well as alternative residues for the variable positions within the sequence. The generic sequences provide an appropriate cysteine skeleton where inter- or intramolecular disulfide bonds can form, and contain certain specified amino acids that may influence the tertiary structure of the folded proteins. In addition, the generic sequences allow for an additional cysteine at position 36 (Generic Sequence 7) or position 41 (Generic Sequence 8), thereby encompassing the biologically active sequences of OP-2 and OP-3.

Generic Sequence 7

```
    Leu Xaa Xaa Xaa Phe Xaa Xaa Xaa Gly Trp Xaa Xaa Xaa Xaa Xaa Xaa
     1               5                  10                  15

Pro Xaa Xaa Xaa Xaa Ala Xaa Tyr Cys Xaa Gly Xaa Cys Xaa Xaa Pro Xaa Xaa
            20                  25                  30

Xaa Xaa Xaa Xaa Xaa Xaa Asn His Ala Xaa Xaa Xaa Xaa Xaa Xaa Xaa Xaa Xaa
 35                  40                  45                  50

Xaa Xaa Xaa Xaa Xaa Xaa Xaa Xaa Cys Cys Xaa Pro Xaa Xaa Xaa Xaa Xaa Xaa
        55                  60                  65                  70

Xaa Xaa Leu Xaa Xaa Xaa Xaa Xaa Xaa Xaa Val Xaa Leu Xaa Xaa Xaa Xaa Xaa
                75                  80                  85

Met Xaa Val Xaa Xaa Cys Xaa Cys Xaa
     90                  95
```

wherein each Xaa independently is selected from a group of one or more specified amino acids defined as follows: "Res." means "residue" and Xaa at res. 2=(Tyr or Lys); Xaa at res. 3=Val or Ile); Xaa at res. 4=(Ser, Asp or Glu); Xaa at res. 6=(Arg, Gln, Ser, Lys or Ala); Xaa at res. 7=(Asp or Glu); Xaa at res. 8=(Leu, Val or Ile); Xaa at res. 11=(Gln, Leu, Asp, His, Asn or Ser); Xaa at res. 12=(Asp, Arg, Asn or Glu); Xaa at res. 13=(Trp or Ser); Xaa at res. 14=(Ile or Val); Xaa at res. 15=(Ile or Val); Xaa at res. 16(Ala or Ser); Xaa at res. 18=(Glu, Gln, Leu, Lys, Pro or Arg); Xaa at res. 19=(Gly or Ser); Xaa at res. 20=(Tyr or Phe); Xaa at res. 21=(Ala, Ser, Asp, Met, His, Gln, Leu or Gly); Xaa at res. 23=(Tyr, Asn or Phe); Xaa at res. 26=(Glu, His, Tyr, Asp, Gln, Ala or Ser); Xaa at res. 28=(Glu, Lys, Asp, Gln or Ala); Xaa at res. 30=(Ala, Ser, Pro, Gln, Ile or Asn); Xaa at res. 31=(Phe, Leu or Tyr); Xaa at res. 33=(Leu, Val or Met); Xaa at res. 34=(Asn, Asp, Ala, Thr or Pro); Xaa at res. 35=(Ser, Asp, Glu, Leu, Ala or Lys); Xaa at res. 36=(Tyr, Cys, His, Ser or Ile); Xaa at res. 37=(Met, Phe, Gly or Leu); Xaa at res. 38=(Asn, Ser or Lys); Xaa at res. 39=(Ala, Ser, Gly or Pro); Xaa at res. 40=(Thr, Leu or Ser); Xaa at res. 44=(Ile, Val or Thr); Xaa at res. 45=(Val, Leu, Met or Ile); Xaa at res. 46=(Gln or Arg); Xaa at res. 47=(Thr, Ala or Ser); Xaa at res. 48=(Leu or Ile); Xaa at res. 49=(Val or Met); Xaa at res. 50=(His, Asn or Arg); Xaa at res. 51=(Phe, Leu, Asn, Ser, Ala or Val); Xaa at res. 52=(Ile, Met, Asn, Ala, Val, Gly or Leu); Xaa at res. 53=(Asn, Lys, Ala, Glu, Gly or Phe); Xaa at res. 54=(Pro, Ser or Val); Xaa at res. 55=(Glu, Asp, Asn, Gly, Val, Pro or Lys); Xaa at res. 56=(Thr, Ala, Val, Lys, Asp, Tyr, Ser, Gly, Ile or His); Xaa at res. 57=(Val, Ala or Ile); Xaa at res. 58=(Pro or Asp); Xaa at res. 59=(Lys, Leu or Glu); Xaa at res. 60=(Pro, Val or Ala); Xaa at res. 63=(Ala or Val); Xaa at res. 65=(Thr, Ala or Glu); Xaa at res. 66=(Gln, Lys, Arg or Glu); Xaa at res. 67=(Leu, Met or Val); Xaa at res. 68=(Asn, Ser, Asp or Gly); Xaa at res. 69=(Ala, Pro or Ser); Xaa at res. 70=(Ile, Thr, Val or Leu); Xaa at res. 71=(Ser, Ala or Pro); Xaa at res. 72=(Val, Leu, Met or Ile); Xaa at res. 74=(Tyr or Phe); Xaa at res. 75=(Phe, Tyr, Leu or His); Xaa at res. 76=(Asp, Asn or Leu); Xaa at res. 77=(Asp, Glu, Asn, Arg or Ser); Xaa at res. 78=(Ser, Gln, Asn, Tyr or Asp); Xaa at res. 79=(Ser, Asn, Asp, Glu or Lys); Xaa at res. 80=(Asn, Thr or Lys); Xaa at res. 82=(Ile, Val or Asn); Xaa at res. 84=(Lys or Arg); Xaa at res. 85=(Lys, Asn, Gln, His, Arg or Val); Xaa at res. 86=(Tyr, Glu or His); Xaa at res. 87=(Arg, Gln, Glu or Pro); Xaa at res. 88=(Asn, Glu, Trp or Asp); Xaa at res. 90=(Val, Thr, Ala or Ile); Xaa at res. 92=(Arg, Lys, Val, Asp, Gln or Glu); Xaa at res. 93=(Ala, Gly, Glu or Ser); Xaa at res. 95=(Gly or Ala) and Xaa at res. 97=(His or Arg).

Generic Sequence 8 (SEQ ID NO: 5) includes all of Generic Sequence 7 and in addition includes the following five amino acid sequences (SEQ ID NO: 8) at its N-terminus:

```
Cys Xaa Xaa Xaa Xaa
 1               5
```

Accordingly, beginning with residue 7, each "Xaa" in Generic Sequence 8 is a specified amino acid defined as for Generic Sequence 7, with the distinction that each residue number described for Generic Sequence 7 is shifted by five in Generic Sequence 8. Thus, "Xaa at res. 2=(Tyr or Lys)" in Generic Sequence 7 refers to Xaa at res. 7 in Generic Sequence 8. In Generic Sequence 8, Xaa at res. 2=(Lys, Arg, Ala or Gln); Xaa at res. 3=(Lys, Arg or Met); Xaa at res. 4=(His, Arg or Gln); and Xaa at res. 5=(Glu, Ser, His, Gly, Arg, Pro, Thr, or Tyr).

In another embodiment, useful morphogenic proteins include those defined by Generic Sequences 9 and 10, defined as follows.

Specifically, Generic Sequences 9 and 10 are composite amino acid sequences of the following proteins: human OP-1, human OP-2, human OP-3, human BMP-2, human BMP-3, human BMP-4, human BMP-5, human BMP-6, human BMP-8, human BMP-9, human BMP10, human BMP-11, *Drosophila* 60A, *Xenopus* Vg-1, sea urchin UNIVIN, human CDMP-1 (mouse GDF-5), human CDMP-2 (mouse GDF-6, human BMP-13), human CDMP-3 (mouse GDF-7, human BMP-12), mouse GDF-3, human GDF-1, mouse GDF-1, chicken DORSALIN, dpp, *Drosophila* SCREW, mouse NODAL, mouse GDF-8, human GDF-8, mouse GDF-9, mouse GDF-10, human GDF-11, mouse GDF-11, human BMP-15, and rat BMP3b. Like Generic Sequence 7, Generic Sequence 9 accommodates the C-terminal six cysteine skeleton and, like Generic Sequence 8, Generic Sequence 10 accommodates the seven cysteine skeleton.

| Generic Sequence 9 |
| --- |
| Xaa Xaa Xaa Xaa Xaa Xaa Xaa Xaa Xaa Xaa Xaa Xaa Xaa Xaa Xaa Xaa (SEQ ID NO:6)<br>1 5 10 15 |
| Pro Xaa Xaa Xaa Xaa Xaa Xaa Xaa Cys Xaa Gly Xaa Cys Xaa Xaa Xaa Xaa<br>20 25 30 |
| Xaa Xaa Xaa Xaa Xaa Xaa Xaa Xaa Xaa Xaa Xaa Xaa Xaa Xaa Xaa Xaa Xaa<br>35 40 45 50 |
| Xaa Xaa Xaa Xaa Xaa Xaa Xaa Xaa Xaa Xaa Xaa Cys Xaa Pro Xaa Xaa Xaa<br>55 60 65 |
| Xaa Xaa Xaa Xaa Xaa Leu Xaa Xaa Xaa Xaa Xaa Xaa Xaa Xaa Xaa Xaa Xaa<br>70 75 80 |
| Xaa Xaa Xaa Xaa Xaa Xaa Xaa Xaa Xaa Cys Xaa Cys Xaa<br>85 90 95 |

wherein each Xaa is independently selected from a group of one or more specified amino acids defined as follows: “Res.” means “residue” and Xaa at res. 1=(Phe, Leu or Glu); Xaa at res. 2=(Tyr, Phe, His, Arg, Thr, Lys, Gln, Val or Glu); Xaa at res. 3=(Val, Ile, Leu or Asp); Xaa at res. 4=(Ser, Asp, Glu, Asn or Phe); Xaa at res. 5=(Phe or Glu); Xaa at res. 6=(Arg, Gln, Lys, Ser, Glu, Ala or Asn); Xaa at res. 7=(Asp, Glu, Leu, Ala or Gln); Xaa at res. 8=(Leu, Val, Met, Ile or Phe); Xaa at res. 9=(Gly, His or Lys); Xaa at res. 10=(Trp or Met); Xaa at res. 11=(Gln, Leu, His, Glu, Asn, Asp, Ser or Gly); Xaa at res. 12=(Asp, Asn, Ser, Lys, Arg, Glu or His); Xaa at res. 13=(Trp or Ser); Xaa at res. 14=(Ile or Val); Xaa at res. 15=(Ile or Val); Xaa at res. 16=(Ala, Ser, Tyr or Trp); Xaa at res. 18=(Glu, Lys, Gln, Met, Pro, Leu, Arg, His or Lys); Xaa at res. 19=(Gly, Glu, Asp, Lys, Ser, Gln, Arg or Phe); Xaa at res. 20=(Tyr or Phe); Xaa at res. 21=(Ala, Ser, Gly, Met, Gln, His, Glu, Asp, Leu, Asn, Lys or Thr); Xaa at res. 22=(Ala or Pro); Xaa at res. 23=(Tyr, Phe, Asn, Ala or Arg); Xaa at res. 24=(Tyr, His, Glu, Phe or Arg); Xaa at res. 26=(Glu, Asp, Ala, Ser, Tyr, His, Lys, Arg, Gln or Gly); Xaa at res. 28=(Glu, Asp, Leu, Val, Lys, Gly, Thr, Ala or Gln); Xaa at res. 30=(Ala, Ser, Ile, Asn, Pro, Glu, Asp, Phe, Gln or Leu); Xaa at res. 31=(Phe, Tyr, Leu, Asn, Gly or Arg); Xaa at res. 32=(Pro, Ser, Ala or Val); Xaa at res. 33=(Leu, Met, Glu, Phe or Val); Xaa at res. 34=(Asn, Asp, Thr, Gly, Ala, Arg, Leu or Pro); Xaa at res. 35=(Ser, Ala, Glu, Asp, Thr, Leu, Lys, Gln or His); Xaa at res. 36=(Tyr, His, Cys, Ile, Arg, Asp, Asn, Lys, Ser, Glu or Gly); Xaa at res. 37=(Met, Leu, Phe, Val, Gly or Tyr); Xaa at res. 38=(Asn, Glu, Thr, Pro, Lys, His, Gly, Met, Val or Arg); Xaa at res. 39=(Ala, Ser, Gly, Pro or Phe); Xaa at res. 40=(Thr, Ser, Leu, Pro, His or Met); Xaa at res. 41=(Asn, Lys, Val, Thr or Gln); Xaa at res. 42=(His, Tyr or Lys); Xaa at res. 43=(Ala, Thr, Leu or Tyr); Xaa at res. 44=(Ile, Thr, Val, Phe, Tyr, Met or Pro); Xaa at res. 45=(Val, Leu, Met, Ile or His); Xaa at res. 46=(Gln, Arg or Thr); Xaa at res. 47=(Thr, Ser, Ala, Asn or His); Xaa at res. 48=(Leu, Asn or Ile); Xaa at res. 49=(Val, Met, Leu, Pro or Ile); Xaa at res. 50=(His, Asn, Arg, Lys, Tyr or Gln); Xaa at res. 51=(Phe, Leu, Ser, Asn, Met, Ala, Arg, Glu, Gly or Gln); Xaa at res. 52=(Ile, Met, Leu, Val, Lys, Gln, Ala or Tyr); Xaa at res. 53=(Asn, Phe, Lys, Glu, Asp, Ala, Gln, Gly, Leu or Val); Xaa at res. 54=(Pro, Asn, Ser, Val or Asp); Xaa at res. 55=(Glu, Asp, Asn, Lys, Arg, Ser, Gly, Thr, Gln, Pro or His); Xaa at res. 56=(Thr, His, Tyr, Ala, Ile, Lys, Asp, Ser, Gly or Arg); Xaa at res. 57=(Val, Ile, Thr, Ala, Leu or Ser); Xaa at res. 58=(Pro, Gly, Ser, Asp or Ala); Xaa at res. 59=(Lys, Leu, Pro, Ala, Ser, Glu, Arg or Gly); Xaa at res. 60=(Pro, Ala, Val, Thr or Ser); Xaa at res. 61=(Cys, Val or Ser); Xaa at res. 63=(Ala, Val or Thr); Xaa at res. 65=(Thr, Ala, Glu, Val, Gly, Asp or Tyr); Xaa at res. 66=(Gln, Lys, Glu, Arg or Val); Xaa at res. 67=(Leu, Met, Thr or Tyr); Xaa at res. 68=(Asn, Ser, Gly, Thr, Asp, Glu, Lys or Val); Xaa at res. 69=(Ala, Pro, Gly or Ser); Xaa at res. 70=(Ile, Thr, Leu or Val); Xaa at res. 71=(Ser, Pro, Ala, Thr, Asn or Gly); Xaa at res. 2=(Val, Ile, Leu or Met); Xaa at res. 74=(Tyr, Phe, Arg, Thr, Tyr or Met); Xaa at res. 75=(Phe, Tyr, His, Leu, Ile, Lys, Gln or Val); Xaa at res. 76=(Asp, Leu, Asn or Glu); Xaa at res. 77=(Asp, Ser, Arg, Asn, Glu, Ala, Lys, Gly or Pro); Xaa at res. 78=(Ser, Asn, Asp, Tyr, Ala, Gly, Gln, Met, Glu, Asn or Lys); Xaa at res. 79=(Ser, Asn, Glu, Asp, Val, Lys, Gly, Gln or Arg); Xaa at res. 80=(Asn, Lys, Thr, Pro, Val, Ile, Arg, Ser or Gln); Xaa at res. 81=(Val, Ile, Thr or Ala); Xaa at res. 82=(Ile, Asn, Val, Leu, Tyr, Asp or Ala); Xaa at res. 83=(Leu, Tyr, Lys or Ile); Xaa at res. 84=(Lys, Arg, Asn, Tyr, Phe, Thr, Glu or Gly); Xaa at res. 85=(Lys, Arg, His, Gln, Asn, Glu or Val); Xaa at res. 86=(Tyr, His, Glu or Ile); Xaa at res. 87=(Arg, Glu, Gln, Pro or Lys); Xaa at res. 88=(Asn, Asp, Ala, Glu, Gly or Lys); Xaa at res. 89=(Met or Ala); Xaa at res. 90=(Val, Ile, Ala, Thr, Ser or Lys); Xaa at res 91=(Val or Ala); Xaa at res. 92=(Arg, Lys, Gln, Asp, Glu, Val, Ala, Ser or Thr); Xaa at res. 93=(Ala, Ser, Glu, Gly, Arg or Thr); Xaa at res. 95=(Gly, Ala or Thr); Xaa at res. 97=(His, Arg, Gly, Leu or Ser). Further, after res. 53 in rBMP3b and mGDF-10 there is an Ile; after res. 54 in GDF-1 there is a T; after res. 54 in BMP3 there is a V; after res. 78 in BMP-8 and Dorsalin there is a G; after res. 37 in hGDF-1 there is Pro, Gly, Gly, Pro.

Generic Sequence 10 (SEQ ID NO: 7) includes all of Generic Sequence 9 (SEQ ID NO: 6) and in addition includes the following sequence (SEQ ID NO: 9) at its N-terminus:

```
Cys Xaa Xaa Xaa Xaa         SEQ ID NO:9
 1               5
```

Accordingly, beginning with residue 6, each “Xaa” in Generic Sequence 10 is a specified amino acid defined as for Generic Sequence 9, with the distinction that each residue number described for Generic Sequence 9 is shifted by five in Generic Sequence 10. Thus, "Xaa at res. 1=(Tyr, Phe, His, Arg, Thr, Lys, Gln, Val or Glu)" in Generic Sequence 9 refers to Xaa at res. 6 in Generic Sequence 10. In Generic Sequence 10, Xaa at res. 2=(Lys, Arg, Gln, Ser, His, Glu, Ala, or Cys); Xaa at res. 3=(Lys, Arg, Met, Lys, Thr, Leu, Tyr, or Ala); Xaa at res. 4=(His, Gln, Arg, Lys, Thr, Leu, Val, Pro, or Tyr); and Xaa at res. 5=(Gln, Thr, His, Arg, Pro, Ser, Ala, Gln, Asn, Tyr, Lys, Asp, or Leu).

As noted above, certain currently preferred bone morphogenic polypeptide sequences useful in this invention have greater than 60% identity, preferably greater than 65% identity, with the amino acid sequence defining the preferred reference sequence of hOP-1. These particularly preferred sequences include allelic and phylogenetic counterpart variants of the OP-1 and OP-2 proteins, including the *Drosophila* 60A protein. Accordingly, in certain particularly preferred embodiments, useful proteins include active proteins comprising pairs of polypeptide chains within the generic amino acid sequence herein referred to as "OPX" (SEQ ID NO: 3), which defines the seven cysteine skeleton and accommodates the homologies between several identified variants of OP-1 and OP-2. As described herein, each Xaa at a given position independently is selected from the residues occurring at the corresponding position in the C-terminal sequence of mouse or human OP-1 or OP-2.

```
    Cys Xaa Xaa His Glu Leu Tyr Val Ser Phe Xaa Asp Leu Gly Trp Xaa Asp Trp
     1               5                  10                  15

Xaa Ile Ala Pro Xaa Gly Tyr Xaa Ala Tyr Tyr Cys Glu Gly Glu Cys Xaa Phe Pro
     20                  25                  30                  35

Leu Xaa Ser Xaa Met Asn Ala Thr Asn His Ala Ile Xaa Gln Xaa Leu Val His Xaa
         40                  45                  50                  55

Xaa Xaa Pro Xaa Xaa Val Pro Lys Xaa Cys Cys Ala Pro Thr Xaa Leu Xaa Ala
             60                  65                  70

Xaa Ser Val Leu Tyr Xaa Asp Xaa Ser Xaa Asn Val Ile Leu Xaa Lys Xaa Arg
 75                  80                  85                  90

Asn Met Val Val Xaa Ala Cys Gly Cys His
         95                  100
```

wherein Xaa at res. 2=(Lys or Arg); Xaa at res. 3=(Lys or Arg); Xaa at res. 11=(Arg or Gln); Xaa at res. 16=(Gln or Leu); Xaa at res. 19=(Ile or Val); Xaa at res. 23=(Glu or Gln); Xaa at res. 26=(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn); Xaa at res. 61=(Thr, Ala or Val); Xaa at res. 65=(Pro or Ala); Xaa at res. 71=(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Ser or Asn); Xaa at res. 89=(Lys or Arg); Xaa at res. 91=(Tyr or His); and Xaa at res. 97=(Arg or Lys).

In still another preferred embodiment, useful morphogenically active proteins have polypeptide chains with amino acid sequences comprising a sequence encoded by a nucleic acid that hybridizes, under low, medium or high stringency hybridization conditions, to DNA or RNA encoding reference morphogenic sequences, e.g., C-terminal sequences defining the conserved seven cysteine domains of OP-1, OP-2, BMP2, BMP4, BMP5, BMP6, 60A, GDF5, GDF6, GDF7 and the like. As used herein, high stringent hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C. Standard stringency conditions are well characterized in commercially available, standard molecular cloning texts. See, for example, *Molecular Cloning A Laboratory Manual,* 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984): *Nucleic Acid Hybridization* (B. D. Hames & S. J. Higgins eds. 1984); and B. Perbal, *A Practical Guide To Molecular Cloning* (1984).

The morphogenic proteins contemplated herein can be expressed from intact or truncated genomic or cDNA or from synthetic DNAs in prokaryotic or eukaryotic host cells. The dimeric proteins can be isolated from the culture media and/or refolded and dimerized in vitro to form biologically active compositions. Heterodimers can be formed in vitro by combining separate, distinct polypeptide chains. Alternatively, heterodimers can be formed in a single cell by co-expressing nucleic acids encoding separate, distinct polypeptide chains. See, for example, WO93/09229, or U.S. Pat. No. 5,411,941, for several exemplary recombinant heterodimer protein production protocols. Currently preferred host cells include, without limitation, prokaryotes including *E. coli*, or eukaryotes including yeast or *Saccharomyces*, or mammalian cells, such as CHO, COS or BSC cells. One of ordinary skill in the art will appreciate that other host cells can be used to advantage. Detailed descriptions of the proteins useful in the practice of this invention, including how to make, use and test them for morphogenic activity, are disclosed in numerous publications, including U.S. Pat. Nos. 5,266,683, 5,011,691, and/or U.S. Pat. No. 5,585,237, the disclosures of which are incorporated by reference herein, as well as in any of the publications recited herein, including any of the U.S. patents, the disclosures of which are incorporated herein by reference.

The dimeric protein species described herein above are referred to herein as "mature" morphogenic proteins. Soluble forms of these proteins also can be created by complexing the dimeric species with part or all of at least one, and preferably two morphogenic protein pro domain peptides. Alternatively, a soluble complex form of a morphogenic protein can be isolated from the cell culture media using the protocol described in WO94/03600, published 18 Feb. 1994, for example. (See below).

Other soluble forms of morphogens include dimers of the uncleaved pro forms of these proteins, as well as "hemidimers" wherein one subunit of the dimer is an uncleaved pro form of the protein, and the other subunit comprises the mature form of the protein, including truncated forms thereof, preferably noncovalently associated with a cleaved pro domain peptide.

As described in published application WO94/03600, the teachings of which are incorporated herein by reference, useful pro domains include the full length pro regions, as well as various truncated forms hereof, particularly truncated forms cleaved at proteolytic Arg-Xaa-Xaa-Arg cleavage sites within the pro domain polypeptide. For example, in OP1, possible pro sequences include sequences defined by residues 30–292 (full length form); 48–292; and 158–292, all of SEQ ID NO: 2. Soluble OP1 complex stability is best enhanced when the pro region comprises the full length form rather than a truncated form, such as the residues 48–292 truncated form, in that residues 30–47 show sequence homology to the N-terminal portions of other morphogens, and currently are believed to have particular utility in enhancing complex stability for all morphogens. Accordingly, currently preferred pro domains include peptides comprising at least the N-terminal fragment, e.g., amino acid residues 30–47 of a naturally occurring morphogen pro domain, or a biosynthetic variant thereof that retains the solubility and/or stability enhancing properties of the naturally-occurring peptide.

As will be appreciated by those having ordinary skill in the art, useful sequences encoding the pro region can be obtained from genetic sequences encoding known morphogens. Alternatively, chimeric pro regions can be constructed from the sequences of one or more known morphogens. Still another option is to create a synthetic sequence variant of one or more known pro region sequences.

Soluble morphogen complexes can be isolated from conditioned media using a simple, three step chromatographic protocol performed in the absence of denaturants. The protocol involves running the media (or body fluid) over an affinity column, followed by ion exchange and gel filtration chromatographies. The affinity column described below is a Zn-IMAC column. An alternative protocol also envisioned to have utility includes an immunoaffinity column, created using standard procedures and, for example, using antibody specific for a given morphogen pro domain (complexed, for example, to a protein A-conjugated Sepharose column). Protocols for developing immunoaffinity columns are well described in the art (see, for example, *Guide to Protein Purification*, M. Deutscher, ed., Academic Press, San Diego, 1990, particularly sections VII and XI thereof).

Morphogens can be expressed in any suitable host cell competent to express recombinant protein. For example, mammalian (CHO, Chinese hamster ovary) cells as described in the art (see, for example, international application US90/05903 (WO91/05802) can be used. The CHO cell conditioned media containing 0.5% FBS is initially purified using Immobilized Metal-Ion Affinity Chromatography (IMAC). The soluble morphogen complex from conditioned media binds very selectively to the Zn-IMAC resin and a high concentration of imidazole (50 mM imidazole, pH 8.0) is required for the effective elution of the bound complex. The Zn-IMAC step separates the soluble morphogen from the bulk of the contaminating serum proteins that elute in the flowthrough and 35 mM imidazole wash fractions. The Zn-IMAC purified soluble morphogen is next applied to an S-Sepharose cation-exchange column equilibrated in 20 mM $NaPO_4$ (pH 7.0) with 50 mM NaCl. This S-Sepharose step serves to further purify and concentrate the soluble complex in preparation for the following gel filtration step. The protein was applied to a Sephacryl S-200HR column equilibrated in TBS. Using substantially the same protocol, soluble morphogens also can be isolated from one or more body fluids, including serum, cerebrospinal fluid or peritoneal fluid.

The soluble complex isolated from cell culture media elutes with an apparent molecular weight of 110 kDa as compared with protein molecular weight standards. The identity of the proteins can be confirmed by N-terminal sequencing. Purity of the final complex can be verified by running the appropriate fraction in a reduced 15% polyacrylamide gel.

As an alternative to purifying soluble complexes from culture media or a body fluid, soluble complexes can be formulated from purified pro domains and mature dimeric species. Successful complex formation apparently requires association of the components under denaturing conditions sufficient to relax the folded structure of these molecules, without affecting disulfide bonds. Preferably, the denaturing conditions mimic the environment of an intracellular vesicle sufficiently such that the cleaved pro domain has an opportunity to associate with the mature dimeric species under relaxed folding conditions. The concentration of denaturant in the solution then is decreased in a controlled, preferably step-wise manner, so as to allow proper refolding of the dimer and pro regions while maintaining the association of the pro domain with the dimer. Useful denaturants include 4–6M urea or guanidine hydrochloride (GuHCl), in buffered solutions of pH 4–10, preferably pH 6–8. The soluble complex then is formed by controlled dialysis or dilution into a solution having a final denaturant concentration of less than 0.1–2M urea or GuHCl, preferably 1–2 M urea of GuHCl, which then preferably can be diluted into a physiological buffer. Protein purification/renaturing procedures and considerations are well described in the art, and details for developing a suitable renaturing protocol readily can be determined by one having ordinary skill in the art. One useful text on the subject is *Guide to Protein Purification*, M. Deutscher, ed., Academic Press, San Diego, 1990, particularly section V. Complex formation also may be aided by addition of one or more chaperone proteins. Stability of the complex also is enhanced by presence of positively charged amino acids, such as arginine.

II. Formulation and Delivery Considerations

General Considerations

The compositions useful in practice of the invention can be formulated using routine methods. All that is required is determination of the desired final concentration of morphogenic protein per administration. Useful formulation methodologies include solubilization of lyophilized protein or analog. Useful protein or analog solubilization solutions include ethanol, urea, physiological and/or acidic buffers, saline buffers, and acetonitrile/trifluoroacetic acid solutions, and the like. See, for example, U.S. Pat. No. 5,266,683. The desired final concentration of protein or analog will depend on the specific activity of the protein or analog as well as the type, volume, and/or anatomical location of the defect. In one preferred embodiment, useful proteins and analogs are those having a half maximal bone forming specific activity of 1.0–2.0 ng molecule/25 mg matrix, or 0.5–1.0 ng protein/25 mg matrix as measured in a standard rat bioassay. Proteins having lower specific activity also can be used to advantage as can morphogen having specific activity in a different tissue morphogens assay. Additionally, the desired final concentration of protein can depend on the age, sex and/or overall health of the recipient. All of these considerations can be evaluated and optimized using the assays enabled by the invention.

Useful morphogen protein or analog dosage ranges are contemplated to include 0.1–1000 mg/kg body weight, preferably in the range of 1–100 mg/kg. As described herein below, protein or analog can be administered systemically as a single bolus or as multiple doses administered over time. Useful concentrations for liquid administration include a range from about 0.5–5000 ml. Optimization of dosages requires no more than routine experimentation and is within the skill level of one of ordinary skill in the art. It should be noted that no obvious morphogenic protein-induced pathological lesions arise when mature protein (e.g., OP1, 20 mg) is administered daily to normal growing rats for 21 consecutive days. Moreover, 10 mg systemic injections of morphogen (e.g., OP1) injected daily for 10 days into normal newborn mice does not produce any gross abnormalities. Toxiaty levels of candidate analogs readily can be determined by the instant invention to determine therapeutically useful dosages.

The protein or analog can be provided to an individual by any means suitable for systemic administration, (e.g., parenterally, as by i.v. or intra peritoneally, or orally). Liquid formulations preferably comprise part of an aqueous, physiologically acceptable solution so that in addition to delivery of the desired protein or analog to a target site, the solution does not otherwise adversely affect the cells' or subject's electrolyte and/or volume balance. Suitable aqueous mediums include, without limitation, normal physiologic saline (e.g., 9.85% NaCl, 0.15M, pH 7–7.4). Such an aqueous solution containing the agent can be made, for example, by dissolving lyophilized protein or dispersing the protein in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. Alternatively, lyophilized protein or analog can be solubilized in sodium acetate buffer (pH 4.5) or its equivalent.

Where the protein or analog is to be provided parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the protein preferably comprises part of an aqueous solution. Currently preferred for intravenous administration of a morphogen is PBS or a sodium acetate buffer. The protein or analog can be administered as a single dose or by periodic injections of a bolus of the protein or analog, or can be made more continuous by intravenous or intraperitoneal administration from a reservoir which is external (e.g., an i.v. bag) or internal (e.g., a bioerodable implant, or a colony of implanted, morphogen/analog-producing cells).

Useful solutions for parenteral administration may be prepared by any of the methods well known in the pharmaceutical art, described, for example, in *Remington's Pharmaceutical Sciences* (Gennaro, A., ed.), Mack Pub., 1990.

Alternatively, the morphogenic protein or analog described herein can be administered orally. Oral administration of proteins as therapeutics generally is not practiced as most proteins are readily degraded by digestive enzymes and acids in the mammalian digestive system before they can be absorbed into the bloodstream. However, the morphogenic proteins described herein typically are acid stable and protease-resistant (see, for example, U.S. Pat. No. 4,968,590). In addition, at least one morphogen, OP1, has been identified in mammary gland extract, colostrum and 57-day milk. Moreover, the OP1 purified from mammary gland extract is morphogenically active and also is detected in the bloodstream. Maternal administration, via ingested milk, may be a natural delivery route of TGFβ superfamily proteins. Letterio et al. (1994), *Science* 264:1936–1938, report that TGFβ is present in murine milk, and that radiolabeled TGFβ is absorbed by gastrointestinal mucosa of suckling juveniles. Labeled, ingested TGFβ appears rapidly in intact form in the juveniles' body tissues, including lung, heart and liver. These findings, as well as those disclosed in the examples below, indicate that oral and parenteral administration are viable means for administering morphogenic proteins systemically to an individual. In addition, while the mature forms of certain morphogenic proteins described herein typically are sparingly soluble, the protein form found in milk (and mammary gland extract and colostrum) is readily soluble, probably by association of the mature, dimeric species with part or all of the pro domain of the intact sequence and/or by association with one or more milk components. See, for example, WO93/0575 1, published Apr. 1, 1993 and U.S. Ser. No. 08/278,730, the disclosure of which is incorporated herein by reference. Accordingly, the compounds provided herein also can be associated with molecules capable of enhancing their solubility in vitro or in vivo.

Another molecule capable of enhancing solubility and particularly useful for oral administrations, is casein. For example, addition of 0.2% casein increases solubility of the mature active form of OP1 by 80%. Other components found in milk and/or various serum proteins also may be useful.

Alternatively or, in addition, orally administered morphogenic protein or analog can be formulated as part of a delivery vehicle competent to be transported through the gastrointestinal system. As one example, the protein can be formulated as part of biologically erodible microsphere, particularly one whose polymers have sufficient adhesive properties to allow temporary interaction with the gastrointestinal mucus and cellular linings and can traverse both the mucosal absorptive epithelium and the follicle-associated epithelium covering the lymptoid tissue of Peyer's patches. Useful polymers include, without limitation, polystyrene, polylactide and/or polyglycolide and/or polycyanoacrylate polymers and combinations thereof, and can be used to transport morphogenic protein across the intestinal lining and into the circulating system. The microspheres described below and in Mathlowitz et al. (1996) *Nature* 386: 410–414, also are considered to be useful. Here polyanhydride copolymers of fumaric and sebacic acid "poly(FA:SA) ", formulated into 20:80 mircospheres (diameter 0.1–10 mm) made, for example by phase inversion nanoencapsulation, traverse both membranes in as little as one hour, as determined by optical microscopy. Still other useful microspheres include polymer blends of poly (fumaric anhydride) and poly (lactide-co-glycolide).

Morphogenic protein or analog readily can be microencapsulated by standard phase inversion protocols. For example, morphogenic protein is added to a dilute polymer solution (i.e., 1–4% w/v in methylene chloride), which then is poured rapidly into an unstirred bath of non-solvent (petroleum ether) at a solvent to non-solvent ratio of 1:100, causing nano and microspheres (0.1–5.0 μm in diameter) to form spontaneously.

The morphogenic proteins and analogs, of course, can be administered systemically alone or in combination with other molecules known to be beneficial in the treatment of the conditions described herein. Thus, in other embodiments the present invention provides assays for evaluating pharmaceutical compositions in which an morphogenic protein or analog is combined with other agents which promote or enhance new tissue formation. In each such composition, the ratios of the morphogenic and mitogenic agents may be adjusted based upon their activities, as disclosed in the literature and as determined through simple experimentation using the methods of the instant invention, to provide a therapeutically effective dosage of each compound in a single unit dosage. The morphogenic and mitogenic agents in such a composition each preferably comprise at least about 1%, and more preferably more than 5% or 10%, of the dry weight of the composition. The compositions can, however, include other pharmaceutical carriers and active agents, as described above and, generally, in *Remington's Pharmaceutical Sciences* (Gennaro, A, ed.), Mack Pub., 1990, and, therefore, the morphogenic and mitogenic agents can each comprise a small fraction of the final weight of the pharmaceutical composition.

Morphogenic formulations readily can be sterilized using standard procedures prior to implantation. For example, proteins conveniently can be filter-sterilized, e.g., using a 0.22 micron filter. Alternatively, chemicals, such as ethylene oxide can be used. Carrier materials, wetting agents and/or binding agents can be sterilized by exposure to chemicals, heat, or ionizing radiation. In addition, morphogenic formulations can be terminally sterilized to a sterility assurance level of $10^{-6}$ by exposure to ionizing radiation, for example, gamma or electron beam radiation. Useful dose ranges include within the range of about 0.5–4.0 megarads, preferably 2.0–3.5 megarads. See, for example, WO 96/40297, published 19 Dec. 1996.

Practice of the invention will be still more fully understood from the following examples, which are presented herein for illustration only and should not be construed as limiting the invention in any way.

IV. Bioassay

A. Bioassay of Bone Morphogenic Activity: Endochondral Bone Formation and Related Properties The art-recognized bioassay for bone induction as described by Sampath and Reddi (Proc. Natl. Acad. Sci. USA (1983) 80:6591–6595) and U.S. Pat. No. 4,968,590, the disclosure of which is herein incorporated by reference, can be used to establish the efficacy of a given device or formulation. Briefly, the assay consists of depositing test samples in subcutaneous sites in recipient rats under ether anesthesia. A vertical incision (1 cm) is made under sterile conditions in the skin over the thoracic region, and a pocket is prepared by blunt dissection. In certain circumstances, approximately 25 mg of the test sample is implanted deep into the pocket and the incision is closed with a metallic skin clip. The heterotropic site allows for the study of bone induction without the possible ambiguities resulting from the use of orthotopic sites. The implants also can be provided intramuscularly which places the devices in closer contact with accessible progenitor cells. Typically intramuscular implants are made in the skeletal muscle of both legs.

The sequential cellular reactions occurring at the heterotropic site are complex. The multistep cascade of endochondral bone formation includes: binding of fibrin and fibronectin to implanted matrix, chemotaxis of cells, proliferation of fibroblasts, differentiation into chondroblasts, cartilage formation, vascular invasion, bone formation, remodeling, and bone marrow differentiation.

Successful implants exhibit a controlled progression through the stages of protein-induced endochondral bone development including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoblastic and bone remodeling on days twelve to eighteen; and (8) hematopoietic bone marrow differentiation in the ossicle on day twenty-one.

Histological sectioning and staining is preferred to determine the extent of osteogenesis in the implants. Staining with toluidine blue or hemotoxylin/eosin clearly demonstrates the ultimate development of endochondral bone. Twelve day bioassays are sufficient to determine whether bone inducing activity is associated with the test sample.

Additionally, alkaline phosphatase activity and/or total calcium content can be used as biochemical markers for osteogenesis. The alkaline phosphatase enzyme activity can be determined spectrophotometrically after homogenization of the excised test material. The activity peaks at 9–10 days in vivo and thereafter slowly declines. Samples showing no bone development by histology should have no alkaline phosphatase activity under these assay conditions. The assay is useful for quantitation and obtaining an estimate of bone formation very quickly after the test samples are removed from the rat. The results as measured by alkaline phosphatase activity level and histological evaluation can be represented as "bone forming units". One bone forming unit represents the amount of protein that is needed for half maximal bone forming activity on day 12. Additionally, dose curves can be constructed for bone inducing activity in vivo at each step of a purification scheme by assaying various concentrations of protein. Accordingly, the skilled artisan can construct representative dose curves using only routine experimentation.

Total calcium content can be determined after homogenization in, for example, cold 0.15M NaCl, 3 mM $NaHCO_3$, pH 9.0, and measuring the calcium content of the acid soluble fraction of sediment.

B. EXAMPLE 1

This assay demonstrates the ability of systemically administered morphogenic protein to induce bone formation at a local defect site. A local, permissive site was created by implanting matrix alone (bovine demineralized, deproteinated bone collagen) at a subcontaneous or intramuscular site in a rat. Bone collagen, when implanted alone in a subcutaneous site, provokes localized inflammation, and rapidly becomes surrounded by migrating mesenchymal stem cells, e.g., progenitor cells that can respond to osteoinductive signals when given locally, to induce new bone formation. Left alone, the induced inflammatory response leads to fibrotic tissue formation at the implant site which can be resolved over time. In the present example, buffer alone, soluble OP-1, or mature OP-1, were administered systemically to evaluate the ability of morphogenic protein to induce new bone formation at the implant locus.

Long-Evans rats each were subjected to four bone collagen implants: Two subcutaneously (left, right sides of thoracic region) and two intramuscularly (one on muscle of each hind leg), as described above (25 mg matrix/implant). Soluble OP-1 (0.5 mg, mature equivalent in PBS buffer) or mOP-1 (0.5 mg in acetate buffer) was administered intravenously (i.v.) through tail vein at time 0, 8, 24, 48 and 72 hours after implantation. The animals were sacrificed on day 12 and examined for new bone formation by histology and biochemical markers. The day of implantation was considered as Day 0. Four groups of four rats each were tested as follows:

| Group | Assay |
|---|---|
| 1) | none |
| 2) | buffer alone; five injections @ 0, 8, 24, 48 and 72 hours (in 500 μl) |
| 3) | sOP-1 (500 μg); five injections @ 0, 8, 24, 48 and 72 hrs (in 500 μl) |
| 4) | mOP-1 (500 μg); five injections @ 0, 8, 24, 48 and 72 hrs (in 500 μl) |

Results.

| Assay | | Histology* | Units alk. phos./ mg protein | μg calcium/ mg tissue |
|---|---|---|---|---|
| negative control: | none | — | <0.1 | <5 |
| | buffer (NaAc) | — | 0.6 | <5 |
| positive control: | matrix + sOP-1 (implant) | +++ | 0.8 | >30 |
| | matrix + mOP-1 (implant) | +++ | 1.5 | >50 |
| systemic admin.: | sOP-1 | +/− | 0.7 | >30 |
| | mOP-1 | ++ | 2.1 | >30 |

*Histology
+++ = >70% bone and cartilage formation
++ = >50% bone and cartilage formation
+/− = >20% bone and cartilage formation
− = <20% bone and cartilage formation

EXAMPLE 2

This example provides a protocol for evaluating the ability of systemically provided protein to target to the local defect site following systemic administration.

In this example, administered protein serum levels are evaluated by standard protocols (Western blot, Elisa, and/or radio-iodination) at times 0 min., 5 min. and 30 min. after injection.

Specifically, mOP-1 (2.5 mg mature in 500 μl of sodium acetate) is administered at 24 h after collagen implant i.v. through tail vein. Appropriate controls include buffer alone. The animals are sacrificed at 5 and 30 min. after OP-1 administration. The implants are extracted in 8 M urea containing detergent buffer and the presence of OP-1 in the implant is examined by Elisa and Western blot analyses. In a second protocol, iodinated OP-1 is provided and radioactive protein measured at the implant site at 5' and 30' post administration.

In order to determine whether systemically-administered OP-1 is available in collagen implants, iodinated OP-1 was administered 24 hours following collagen implantation. The implants were then harvested 5, 15, and 60 minutes after administration of the labeled OP-1. Adjacent subcutaneous fascia and thigh skeletal tissue were harvested as controls. SDS-PAGE autoradiography analysis of extracted tissue proteins demonstrated that a portion of the iodinated OP-1 was detectable in the collagen implants harvested at 5 minutes, but was not detectable in the implants harvested at 15 or 60 minutes. Control samples did not contain detectable levels of labeled OP-1 at any time interval. Previous pharmacokinetic studies have shown that about 0.5% of intraveneously-administered OP-1 is available in circulation within one minutes, and is cleared from circulation with a half-life of about 15–30 minutes. It is likely that a portion of the OP-1 detectable at 5 minutes following iv administration is sufficient to trigger differentiation of endochondral bone.

Tests showed that bovine bone-derived insoluble type I collagen is superior to other insoluble collagens obtained from rat tail tendon, bovine achilles tendon and type IV collagen-enriched matrigel. Hydroxyapatite was also less effective as a carrier. Surgical wound sites without a collagen implant showed no signs of bone formation, indicating that collagen implants are required to recruit mesenchymal cells locally in order to respond to OP-1 signal upon systemic administration.

EXAMPLE 3

This example demonstrates that a single dose of systemically administered morphogenic protein is competent to induce new tissue formation at a locale permissive defect site distal to the site of administration, and that therapeutic effect is not time-sensitive. Specifically, morphogenic protein, administered as a single bolus at twenty-four or fourty-eight or seventy-two hrs. induces new bone formation in the rat bioassay, at levels comparable to those seen with multiple injections.

In these studies OP-1 was administered systemically at a single concentration (500 μg in 500 μl, given 5 injections @ 0. 6, 24, 48 and 72 hrs. after collagen matrix implantation, as shown in Example 1, or single administration of 500 μg of OP-1 at any given time). Control groups (none and buffer injected) did not induce bone formation at the collagen implant sites (s.c. or i.m.) whereas mature OP-1 injected groups induced endochondral bone, as examined after 12 days.

Long-Evans (6 wks old) were subjected to subcutaneous and intramuscular implants as detailed above. The implants consisted of bovine collagenous matrix (approximately 25 mg) only, implanted at subcutaneous site on both side of the rats, and at skeletal muscle of both legs. Four implants were made per rat, with four rats per group. The day of collagen implant or OP-1 administration is considered as Day 0 and Time 0 hrs.

This example demonstrates the ability of a single dose to affect new bone formation in a mammal, and that the dose can be administered at long times after the defect has been created. Specifically, systemically administered morphogenic protein is effective even when provided after the onset or initiation of fibrotic tissue formation.

By seventy-two hours post trauma the microenvironment of a local defect site has normalized and stabilized. Specifically, microvessals have been repaired, any inflammatory response triggered by the surgery or trauma has stabilized, and fibroblasts now are present at the site and can initiate the laying down of extracellular matrix scarring tissue. Thus, in the absence of morphogenic protein, by seventy-two hrs. post implant the micro environment of a test implant now substantially mimics that of a refractory healing site in a compromised individual, e.g., an individual whose ability to form new bone callus is compromised by, for example, age, disease (for example, diabetes, osteoporosis), therapeutics used in association with surgical or other therapeutic procedures (steroids, for example). The ability of systemically administered morphogenic proteins to induce new bone formation when administered at times substantially after the defect has been created has positive implications for treating patients suffering from refractory healing.

Figure 2:
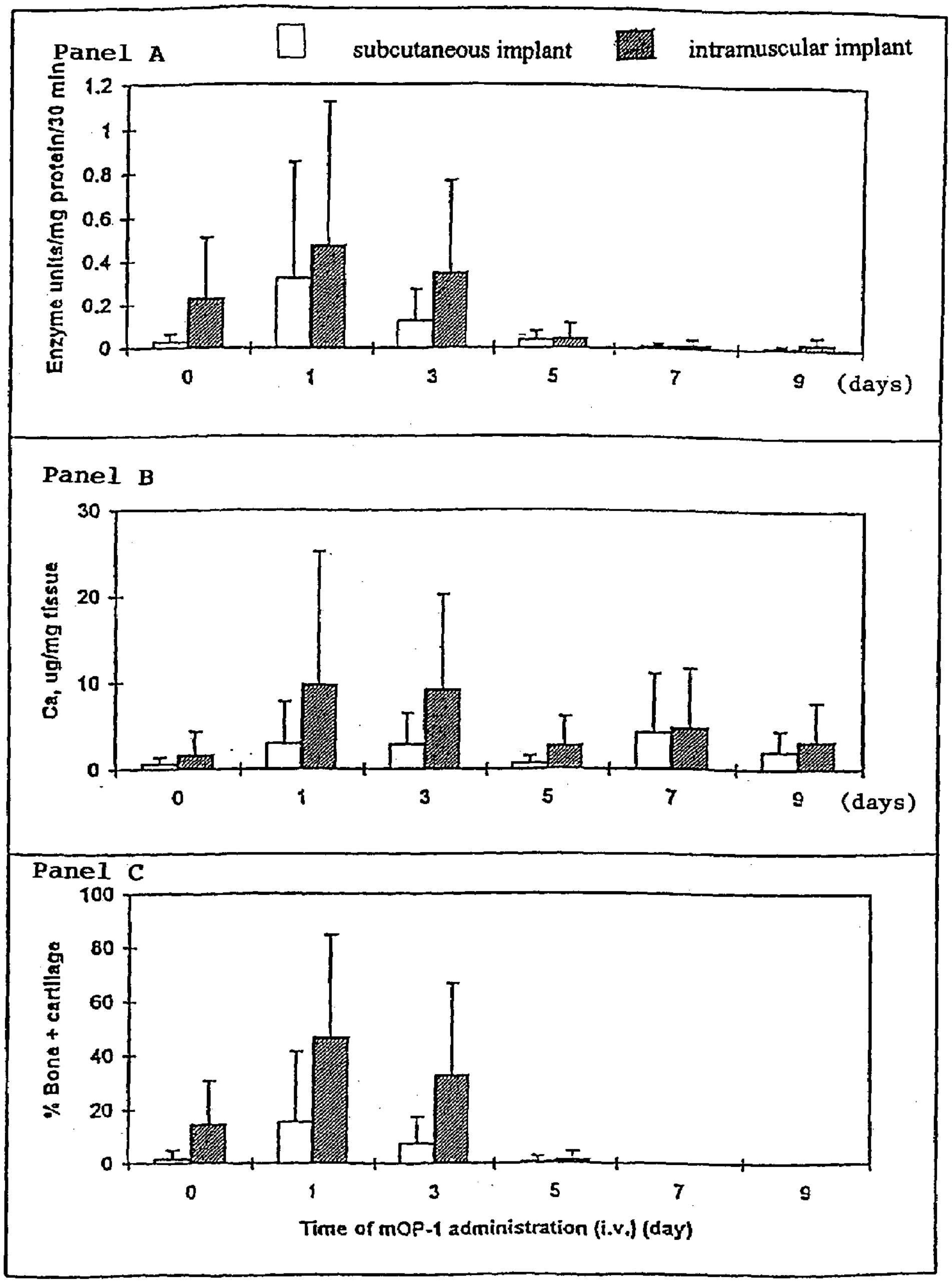
FIGS. 2A–2C is a graph showing the effect of timing of OP-1 administration on bone forming activity. Bovine collagen carrier (25 mg) was implanted at subcutaneous sites (open bar) and intramuscular sites (filled bar), and OP-1 was administered via the tail vein (1500 ug as a single injection) 1, 3, 5, 7, or 9 days after collagen implantation. Bone forming activity was determined by histology (Panel 2C), the amount of alkaline phosphatase induced (Panel 2A), and calcium content of the implant (Panel 2B) at 12 days after administration of OP-1. See Example 3 for experimental details.

Osteogenesis induced by OP-1 (2.5 mg/rat), as measured by determined by the amount of alkaline phosphatase induced (Panel 2A), calcium content of the implant (Panel 2B), and histology (Panel 2C) was maximal when OP-1 was administered 24 or 72 hours after collagen implantation. An approximately 30% reduction in osteogenesis was observed when OP-1 was administered 6 hours after implantation. FIG. 2A–2C shows these results for implants at subcutaneous sites (open bar) or intramuscular sites (filled bar). In each case, OP-1 was administered at the time point indicated, and osteogenesis was measured at day 12 after OP-1 administration. At times longer than 120 hours (i.e. 5 days) post-implantation OP-1 failed to induce bone, suggesting that collagen may have already been committed to fibroblast lineages, and therefore non-responsive to OP-1.

EXAMPLE 4

This example demonstrates that bone formation is dependent on the dose of systemically administered morphogenic protein. Specifically, in this assay mOP-1 (0.05, 0.5, 2.5 mg in 500 μl acetate buffer) and soluble OP-1 (0.05, 0.5, 2.5 mg mature equivalent in PBS) were administered (at 24 h after collagen implant) i.v. through tail vein. Appropriate controls include buffer (sodium acetate) alone. The animals were sacrificed on day 12 after OP-1 administration and examined for new bone formation by histology, alkaline phosphatase activity and calcium content. Long-Evans (4–5 wks old) were subjected to subcutaneous and intramuscular implants as detailed above. Four implants per rat and four rats per group. The day of OP-1 administration is considered as Day 0 and Time 0 hrs.

Results. Control groups (buffer injected) did not induce bone formation at the collagen implant sites (s.c. or i.m.) whereas mature OP-1 injected groups induced endochondral bone, as examined after 12–14 days. The bone forming activity exhibited by the group that received multiple injections is comparable to that observed in Example 1. The amount of bone forming activity observed in the groups that received single administration was directly related to the dosing of OP-1; with the maximum activity observed in high concentration of OP-1 (2.5 mg), and exhibiting bone forming activity comparable to that observed in Example 1.

Groups that received a single administration of OP-1 at 24 h after collagen implant, all exhibited bone formation, with the higher dose group (2.5 mg) showing bone formation comparable to the group that received multiple injections; and the low concentration (50 or 500 ug) groups showing endochondral bone formation in 50 or 60% of the implants respectively. Since all implants from groups that received multiple or a single high dose administration formed bone comparable to each other, the amount of bone formed by the systemic administration is not dependent on the dosing regiment. Based on the rat bioassay, a currently preferred dose range for effecting osteogenesis in a rat by single dose systemic administration lies in the range of about 0.5 to 2.5 mg per rat, or 1–50 or 5–25 mg/kg body weight. It will be appreciated that determining preferred dosages for treating individuals can be determined by routine experimentation.

In related experiments, single doses (2.5 mg OP-1/rat) administered at 24 hr. post implant were evaluated at days 3, 5, 7, 9, 11, 14, 21, 28 and 60 to determine the rate and quality of new bone (callus) formation. The animals were sacrificed on days 3, 5, 7, 9, 11, 14, 21 and 28 and 60 after OP-1 administration and examined for new bone formation by biochemical assays and by histology. Data show good bone formation by 1 week and that bone formation follows the same biology of locally provided protein, namely a conserved progression through the commitment steps evidencing true bone formations; including recruitment of mesenchymal progenitor cells, proliferation of chondrocytes, matrix deposition, osteoblast recruitment and proliferation; remodeling, and bone marrow formation.

In a separate experiment, the potential of systemically-administered morphogenic proteins to initiate new bone formation at local ectopic sites where collagen carrier alone was implanted. Approximately 25 mg each of bovine bone-derived insoluble type I collagen was implanted at subcutaneous (left and right side of thoracic region) and intramuscular (left and right thigh skeletal muscle) sites of 6–8 week old Long-Evans male rats. Four rats per group were used. OP-1 (500 ul) was given intravenously through the tail vein at concentrations of 0.05, 0.5, 1.25, and 2.5 mg/rat. Groups receiving buffer with a collagen implant and systemic OP-1 with a mock implant were used as controls. Osteogenic activity was determined by histology, alkaline phosphatase activity, and calcium content at day 12 after OP-1 administration.

FIG. 1 shows that intravenously administered OP-1 induces new bone formation in a dose-dependent manner as measured by alkaline phosphate activity, calcium content, and histologic examination of implants harvested on day 12 after OP-1 administration. Maximal bone-forming activity was observed when a dose of 2.5 mg OP-1/rat was used. About 30% maximal activity was observed when 0.05 mg OP-1/rat was used. A single administration of 2.5 mg OP-1 given in one injection (24 hours post-implant), produced comparable bone-forming activity as 5 injections administered at 0, 8, 24, 48, and 72 hours after implantation produced comparable bone-forming activity. Importantly, the amount of OP-1 administered systemically to effect maximal bone formation is about 1000-fold higher than the amount necessary to induce bone formation when the collagen/OP-1 device is used to induce bone locally. Collagen implants at intramuscular sites appear to work better than those at subcutaneous sites, as responding cells and vascular components are readily available at intramuscular sites.

EXAMPLE 5

The following example provides a protocol for comparative measurement of bone formation where protein is provided by any systemic route, namely: i.v., intraperitoneal or by oral administration. Liquid solutions of OP-1 were used for all administration routes as follows.

Intravenous and Intraperitoneal: 500 μg (mature equivalent) dose administered at 0, 6, 24, 48 and 72 h (in 500 μl volume) after collagen implant. Oral administration: soluble and mature OP-1, administered as one time doses of 2.5 mg in 1–2 ml at 24 h. With respect to i.v. and oral administration mOP-1 is taken in sodium acetate buffer for i.v. administration and in 0.1% casein in PBS for oral administration. OP-1 is completely soluble in 0.1% casein. The day of OP-1 administration is considered as day 0 and implants harvested on day 12. The systemic OP-1 induced osteogenesis in the collagen implant then is evaluated based on the specific activity of alkaline phosphatase, calcium content and histology.

Alternative Oral Administration Protocol: 2.5 mg protein (mature OP-1) solubilized in dilute methylene chloride and confined polymer solution (i.e., FA:SA, 20:80) and encapsulated by phase inversion.

Results: It is anticipated that all three routes will induce osteogenesis at the test implant site. The methodology provides means for assaying preferred dosages and formulations for a desired administration route.

Histochemical and biochemical analyses show that bone formation induced by systemically-administered OP-1 in local collagen implants undergoes a similar cascade of cellular events as that induced by local OP-1/collagen implants.

EXAMPLE 6

This example demonstrates the ability of other systemically administered morphogenic proteins to induce local bone formation. Using the protocols described above, recombinant BMP-2, CDMP-1 and CDMP-2 were evaluated. In the assay OP-1, BMP-2 (at 1.25 mg) and CDMP-1 and CDMP-2 (at 2.5 mg) were administered systemically (tail vein, 500 μl) at 24 hrs after collagen implant. The day of protein administration was considered as day 0 and implants were harvested on day 12.

EXAMPLE 7

This example evaluates the effect of the age of the animal on osteogenesis in the collagen implants at ectopic sites and the ability of systemically administered morphogenic protein to accelerate or improve healing in adult rats. Typically, juvenile rats heal faster than aged rats. For example, when hair line fractures are induced in juvenile rats (e.g., 1 month old), callus formation can be seen by one week, and complete healing occurs by three weeks. By contrast, in adult rats (24 months old) formation takes two weeks and complete healing requires 6–12 weeks.

Long-Evans or Fisher rats at 1, 3, 6, 12 and 24 months old were subjected to subcutaneous and intramuscular implants as detailed above. The implants consisted of bovine collagenous matrix (approximately 25 mg) only. Four implants were made per rat, with four rats per group. Mature OP-1 was administered at 0, 6, 24, 48 and 72 hrs at 500 μg per 500 μl in acetate buffer. The day of OP-1 administration is considered as Day 0. Animals were evaluated at selected time points within the following day range: days 3, 5, 7, 9, 11, 14, 21, 28 and 60.

Results: Systemically administered morphogenic protein resulted in faster callus and bone formation in older rats as compared with controls. The data demonstrates the utility of systemic administration as a means for enhancing bone repair in adults or any individuals having a reduced capacity for bone healing and who experience refractory healing. Such individuals have a reduced or delayed ability to repair fractures either because of a lack of precursor cells, poor vascularity, reduced inductive signals or the like.

A comparison of OP-1 effects with related members of the morphogen family shows that OP-1 is more potent than BMP-2, CDMP-1 (GDF-5), and CDMP-2 (GDF-6) in inducing osteogenesis upon systemic administration as measured by calcium content and histology performed on day 12 implants.

Figure 3A:
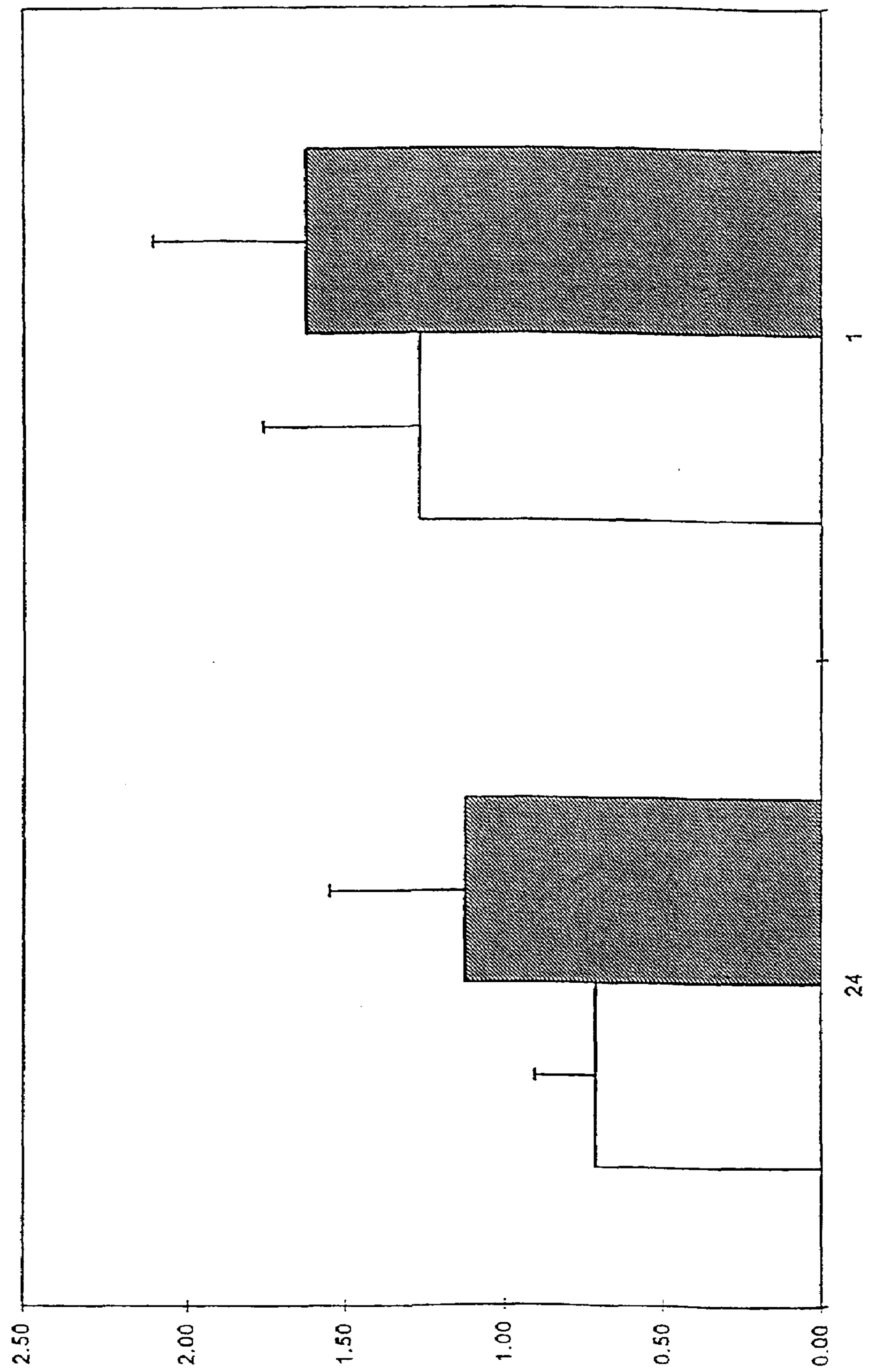
FIGS. 3A–3B shows the effect of the age of an animal on bone-forming activity induced by systemically-administered OP-1. Bovine collagen carrier (25 mg) was implanted at subuctaneous sites (open bar) and intramuscular sites (filled bar). OP-1 was administered via the tail vein (2500 ug as a single injection) 24 hours after carrier implantation. Bone-forming activity was determined by alkaline phosphatase activity (Panel 3A), calcium content (Panel 3B), and by histology conducted on implants at 12 days after OP-1 implantation. See Example 7 for experimental details.
Figure 3B:
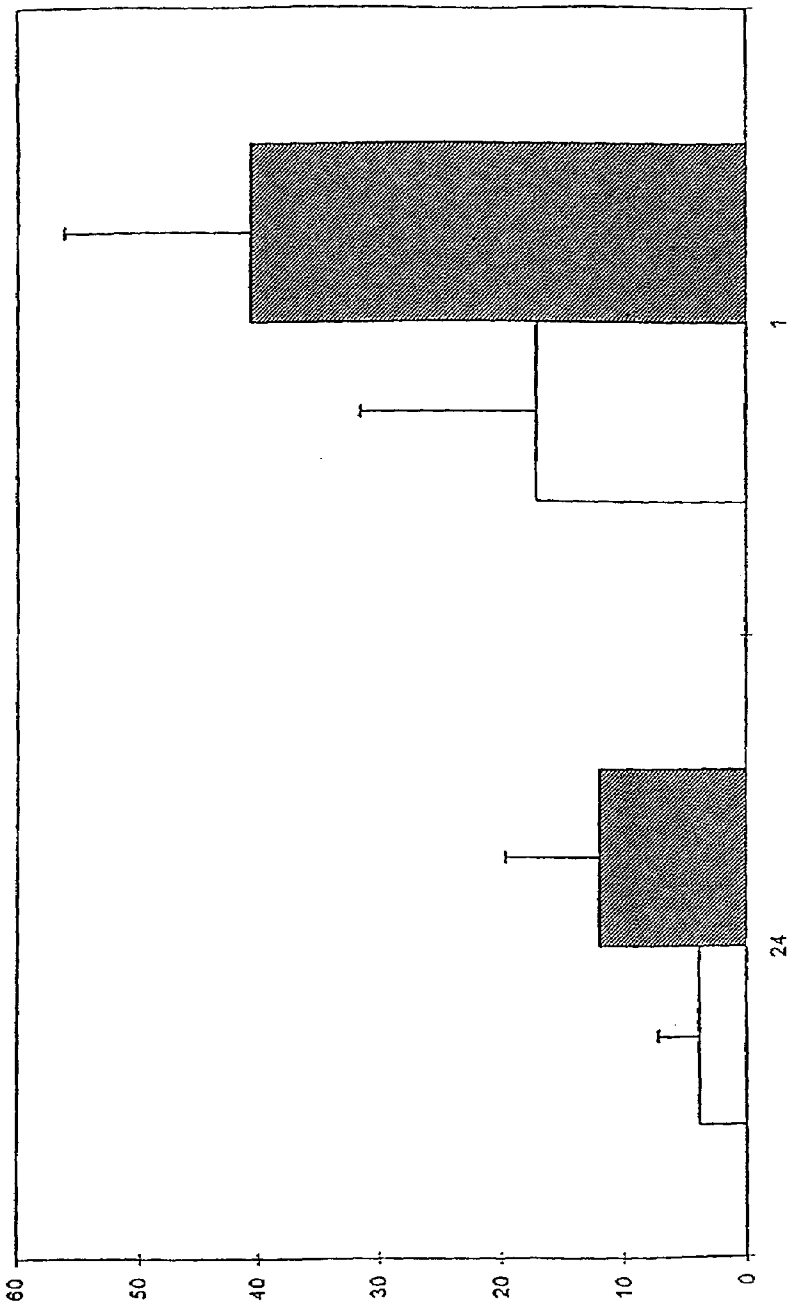

The effect on osteogenesis at local collagen implant sites in animals given OP-1 systemically was independent of age. Results are shown in FIGS. 3A–3B. The effect of OP-1 was determined on 24-months old, i.e., adults, rats (left set of bars) and on 1-month old, i.e., juvenile, rats (right set of bars), which received collagen implants at subcutaneous sites (open bar) or intramuscular sites (filled bars). The bone-forming activity was determined by alkaline phosphatase activity (Panel 3A) and by calcium content (Panel 3B). As shown in Panel 3B there was some delay in the rate of bone remodeling and mineralization as determined by calcium content.

EXAMPLE 8

This example demonstrates the ability of systemically administered morphogenic protein to induce osteogenesis in a critical size ulna segmental defect in an art-recognized canine model. A critical size bone defect is incapable of spontaneous healing, and demonstrates the ability of morphogenic protein to induce new tissue formation permissive locus in a typically nonregenerating tissue. Briefly, adult male mongrel dogs, supplied by authorized kennels, are utilized because their well-known bone repair and remodeling characteristics Animals preferably are at least two years old and weigh from 40 to 50 pounds, with special attention was paid in selecting animals of uniform size and weight to limit the variability in bone geometry and loading. Bilateral 2.5 cm ulna segmental defects are created in individual dogs using standard surgical procedures. All right side defects are left untreated, all left side defects receive the standard morphogenic protein device using, for example, recombinant human morphogenic protein-1 (rhOP-1) admixed with bovine bone Type I collagen matrix at a ratio of 2.5 mg rhOP-1 per gram of collagen matrix. Mature or soluble morphogenic protein is administered in dose ranges of 0.5 mg–5 mg (500–1,000 ml), administered as a single bolus at least at 24 hrs, 48 hrs, or 72 hrs post surgery, or as a series of five separate injections as described above. Control groups include no systemically administered morphogenic protein, a mock implant; and animals subjected to a single test defect, treated either with a standard device or systemically administered protein. Biweekly radiographs are taken to study the progression of healing and graded on a 0–6 scale. At sacrifice, all ulnae are retrieved en bloc, and those that are healed sufficiently upon manual manipulation are mechanically tested in torsion. Segments then are evaluated by histology for tissue response, bone architecture and remodeling, and quality and amount of new bone formation and healing. It is anticipated that systemically administered morphogenic protein will induce osteogenesis sufficient to repair the ulna defect.

EXAMPLE 9

Provided below is a standard animal pulmonary fibrosis model and can be used to demonstrate the ability of systemically administered morphogens to repair damaged lung tissue. The example essentially follows the methods described in Haston et al. (1996) *Cancer Research* 56: 2596–2601; Weinbach et al. (1996) *Cancer Research* 56: 5659–5665; Harrison et al. (1988) *J. Pharmacol. Exp. Thr.* 247: 1052–1058.

Pulmonary fibrosis is a potentially lethal, chronic response of the lung to injury caused by bleomycin (BLM), a highly useful antineoplastic agent that lacks substantial bone morrow toxicity. The hallmark of this disorder is characterized by an increased deposition of extracellular matrix proteins in the alveolar wall, notably collagen, which compromises pulmonary function.

In the assay, lung damage is induced in commercially available laboratory mice with BLM injections, typically 100, 300, 400 or 500 mg/kg. The agent can be administered by interperitoneally or subcutaneous injections, or by means of an implanted pump. Preferably, the $C_{57}$BL/6J mouse strain is utilized (Jackson Laboratoryies), which has a fibrosis-prone phenotype, e.g., histological lesions and increased pulmonary OH-praline content characteristic of pulmonary fibrosis. A fibrosis-resistant phenotype strain, such as $C_3$hf/kam can be used as a control strain.

In the example, buffer alone, mature morphogen or the soluble complex form are administered in one or more of the following protocols:

A. Single bolus (0.05, 0.5, 1.0, or 2.5 mg/500 ml) administered in 500 μl volumes at 0, 6, 12, 24, 48 or 72 hours after BLM injection.

B. Multiple injections up to a total of (0.05, 0.5, 1.0 or 2.5 mg), administered in 500 μl volumes at time 0, 6, 24, 48, and 72 hours.

The animals are sacrificed by cervical dislocation at 8, 10 or 12 weeks or when in respiratory distress as indicated by an elevated breathing rate. The lungs then are evaluated by histology and OH-proline content using standard methodologies.

The results are expected to demonstrate that, in the absence of morphogenic protein, fibrosis is induced by moderate doses of BLM (cumulative dose, 300 or 400 mg/kg). In contrast mice treated with systemically administered morphogens show substantially reduced or no fibrotic lesions of fibrosis and these mice tolerate higher i.p. -inoculated doses of BLM.

EXAMPLE 10

Myocardial infarcts heal by scarring because myocardium cannot regenerate. This assay demonstrates the ability of systemically administered morphogens to regenerate new contractile tissue, and substantially restore function. The assay follows the protocol of Murry et al. (1996) *J. Clin. Invest* 98(11): 2512–2523.

Hearts of adult inbred rats are injured by a standard freeze-thaw, methodology. Specifically, a 1-cm-diameter aluminum rod, precooled with liquid nitrogen, is placed in direct contact with the anterior left ventricle for 15 seconds. Freeze-thaw reproducibly causes a disc-shaped region of coagulation necrosis, ~1 cm in diameter, extending ~2 mm into the myocardium. Morphogen or saline buffer alone is administered at time t=0, 6, 24, 48 and 72 hours after injury. Morphogen can be administered as a single bolus or by multiple injections, as described in Example 10. By 1 week, multimucleated myotubes are evident in repairing tissue. At 2 wks, satellite stem cells are evident. By 7 weeks β-MHC expression is detected.

At 1, 2 and 7 weeks and myocardium tissue formation evaluated by histology and standard biochemical marker assays, including evidence of β-MHC expression.

EXAMPLE 11

Morphogen Expression in Regenerating Liver Tissue Following Toxin-Induced Tissue Damage Hepatic tissue repair following toxic agent-induced damaged tissue involves proliferation and differentiation of hepatocyte precursor cells. This tissue reparation apparently mimics the tissue morphogenesis cascade that occurs during embryogenesis (Fausto, et al.(1989) *Lab. Investigation* 60:4–13). As demonstrated in the example below, systemically administered morphogen can enhance hepatic tissue regeneration following galactosamine or carbon tetrachloride ($CCl_4$)-induced liver damage. Experiments are performed essentially as described in Kuhlmann et al., (1980) *Virchows Arch* 387:47–57, the disclosure of which is incorporated herein by reference.

galactosamine-HCl 0.75 g/.kg body weight on day 0. Morphogen is administered In this experiment, male rats were provided with a single intraperitoneal injection of systemically (e.g., i. vaccording to the following protocol: 0.5, 1.0 or 2.5 mg m OP-1 in 500 μg buffer (acetate or PBS), at 6, 12, 24 or 48 hours post toxin injection. Animals are sacrificed on days 3, 5, 12, 20, and evaluated by histology.

EXAMPLE 12

Morphogen-Induced Liver Regeneration

This Example demonstrates the ability of systemically administered morphogen to regenerate new liver tissue following a partial hepatectomy.

While hepatocytes have a remarkable capacity to undergo compensatory growth following tissue loss, the reparative properties of liver differ significantly from embryonic morphogenesis. Specifically, following a partial hepatectomy wherein a liver lobe is partially or completely removed, the remaining intact lobes grow rapidly and double in weight due to the ability of the differentiated hepatocytes in the intact lobe to undergo limited proliferation. However, the excised lobe itself is not regenerated. The following example demonstrates the ability of morphogens to regenerate lost hepatic tissue following a partial hepatectomy, including regenerating the excised tissue lobe. The protocol described below is a variation on a standard partial hepatectomy protocol, described, for example, by Higgins et al. (1931) *Arch. Pathol.* 12:136–202 and Braun et al. (1989) *PNAS* 86:1558–1562, the disclosures of which are incorporated herein by reference.

Growing rats or aged rats are anesthetized by using ketamine. Two of the liver lobes (left and right) are cut out (approximately ⅓ of the lobe). The wound is closed using standard surgical procedures. Morphogen, e.g., purified recombinant human OP-1, mature form, is administered systemically intravenously (i.e.) or p. (interitoneally). OP-1 (mature or soluble) is injected at 0.5, 1.0 or 2.5 mg protein in 500 μl buffer (acetate or PBS), at times 12, 24, 48 or 72 hours post surgery. Placebo samples are injection buffer without morphogen. Following surgery the rats are allowed to eat normal food and drink tap water.

After 12 days, the rats are sacrificed and liver regeneration is observed visually. OP-1 injected group(s) will show complete liver tissue regeneration including reformation of the excised lobe tissue, and show no substantial sign of any cut in the liver. By contrast, in the control group into which only PBS is injected, the excised lobe tissue is not substantially regenerated. The original incision typically remains in this sample.

In a variation on this example, morphogen is administered as a series of injections over a period of 3–10 days following surgery.

EXAMPLE 13

Morphogen Treatment of Oral Mucositis

Oral mucositis involves ulcerations of the mouth as a consequence of, e.g., radiation therapy or chemotherapy. The course of ulcerative mucositis may be divided into a destructive phase and a healing phase. Since the cells of the basal layer of the oral epithelium divide at a rapid rate, they are susceptible to the antimitogenic and toxic effects of chemotherapy. As a result, atrophic changes occur which then are followed by ulceration. This constitutes the destructive phase. Following ulcer formation, the lesions slowly resolve during the healing phase.

The example below demonstrates the efficacy of systemically administered morphogen in protecting the oral mucosa from oral mucositis in a hamster model, including both inhibiting ulceration and enhancing regeneration of ulcerated tissue. Systemic administration eliminates problems associated with maintaining topically applied morphogen at a defect locus.

Details of the protocol can be found in Sonis, et al., (1990) *Oral Surg. Oral Med. Oral Pathol* 69: 437–443, the disclosure of which is incorporated herein by reference.

Briefly, golden syrian hamsters (6–8 wks old, Charles River Laboratories, Wilmington, Mass.) are divided into test groups: a placebo (e.g., saline) control, and a morphogen low dose group (100 ng) and a morphogen high dose group (1 μg), Groups 2 and 3, respectively. Additional groups can modulate the number of injections morphogen is (single bolus vs. multiple administration). Each group contain the same number of animals. Beginning on day 0 and continuing through day 5 morphogen is administered systemically (mature form) (oral, or ip, or iv; (tail vein)). On day 3, all groups begin the mucositis-induction procedure. 5-fluorouracil is injected intraperitoneally on days 3 (60 mg/kg) and 5 (40 mg/kg). On day 7, the right buccal pouch mucosa is superficially irritated with a calibrated 18 gauge needle. In untreated animals, severe ulcerative mucositis is induced in at least 80% of the animals by day 10.

On day 12, two animals in each group are sacrificed for histological studies. The right buccal pouch mucosa and underlying connective tissue are dissected and fixed in 10% formalin using standard dissection and histology procedures. The specimens are mounted in paraffin and prepared for histologic examination. Sections then are stained with hematoxylin and eosin and are examined blindly by three oral pathologists with expertise in hamster histology and scored blind against a standard mucositis panel. The extent of atrophy, cellular infiltration, connective tissue breakdown, degree of ulceration and epithelialization are assessed.

Based on histology, administered morphogen inhibits lesion formation significantly in a dose-dependent manner. By contrast, significant tissue necrosis, indicated by the dark regions in the tissue, and ulceration, indicated by the light globular areas in the tissue, is evident in untreated pouches. The morphogen-treated tissue shows healthy tissue with no necrosis and little or no ulceration. Single administration of high doses are contemplated to be substantially as effective as multiple injection doses.

The method of the invention allows an individual at risk to take the protein prophylactically, concurrent with a cancer therapy regimen allowing morphogen to be present in the system when at the time the initial oral mucositis defect occurs.

EXAMPLE 14

Morphogen Treatment of Duodenal Ulcer Formation

The following example provides a rat model for demonstrating the efficacy of systemically administering morphogen in treating duodenal ulcers. A detailed description of the protocol is provided in Pilan et al., (1985) *Digestive Diseases and Sciences* 30: 240–246, the disclosure of which is incorporated herein by reference. Briefly, Sprague-Dawley female rats (e.g., Charles River Laboratories, 150–200 grams) receive the duodenal ulcerogen cysteamine-HCl at a dose of 25–28 milligrams (mg) per 100 grams (gm) of body weight orally by intragastric gavage 3 times on the same day. Additionally, cortisol is administered subcutaneously to each rat at a single dose of 5 mg of cortisol to 100 gm of body weight to decrease the mortality resulting from the administration of the cysteamine-HCl.

Three days after administration of the cysteamine-HCl, rats having penetrating and perforating duodenal ulcers are identified by standard laparotomy and randomized into control and morphogen-treated groups.

The rats of Group 1, all of which have ulcers, receive no morphogen and are treated only with saline. The rats of Group 2 each of which also have ulcers, receive 50–100 ng of morphogen per 100 gm of body weight administered i.v. (k.l vein) or i.p. or by oral administration. Group 3 rats, all of which have ulcers, receive 200–500 ng of morphogen per 100 gm of body weight. Treatments also can be a single bolus or a series of multiple injections, as described in Example 10. Animals are sacrificed on day 21, and the ulcers measured and histologic sections taken.

Histology of duodenal sections from morphogen-treated animals shows healed ulcers with prominent and dense granulation tissue and partial or complete re-epithelialization, demonstrating that oral administration of morphogen can significantly accelerate the healing of ulcers of the GI tract. Moreover, treatment with morphogen before or concomitantly with ulceration also inhibits ulcer formation.

EXAMPLE 15

Morphogen Treatment of Retinal Disorders

Systemically administered morphogen also can be used to treat retinal disorders, particularly for treatment of macular degeneration and holes, where it is anticipated to promote healing and significantly improve vision. The treatment also can be used on retinal holes, tears, and detachment. These disorders are characterized by loss of visual acuity.

Eyes to be treated with morphogen undergo complete pre- and post-operative ocular examination including visual acuity testing, intraocular pressure measurements, slit-lamp bio-microscopy, and binocular indirect ophthalmoscopy. Surgical strategy will vary dependent upon the exact vitreoretinal anatomy, as is known in the art. Generally, all vitrectomies are performed with standard three-port instrumentation using standard procedures. Vitrectomy is performed prior to morphogen administration.

Morphogen is administered systemically (ip., iv) following vitrectomy recording to the protocol outlined in Example 10, or a variation thereof. Animals are sacrificed at 1 week, 2 weeks, 7 weeks and evaluated by histology. Systemically administered morphogen eliminates the need to provide morphogen by local injection and is anticipated to promote reattachment of the retina and regeneration of lost retinal tissues at least as well as locally provided protein. In addition, systemic administration of morphogen should inhibit reproliferation of fibrovascular tissue, and inhibit neovascularization.

Morphogen similarly can be administered to treat macular holes. Such treatment is expected to provide improvement of vision and healing by decreasing the thickness of the edge of the hole.

EXAMPLE 16

This example demonstrates the ability of systemically administered osteogenic protein to correct an osteochondral or chondral defect, using an art-recognized animal model (dog). Specifically, a study using a standard dog osteochondral plug defect model is conducted as described below. Briefly, full thickness defects 5 mm in diameter and extending 6 mm into the subchondral bone are created bilaterally on the medial femoral condyle of 4 adult mongrel dogs using standard surgical procedures and animals supplied by authorized kennels. The left side defects receive standard osteogenic device and the right side defect is left untreated. Systemic administration assays are carried out as for the critical site defect in Example 8 above, with appropriate controls, including mock implants. That is, a range of useful dosages are evaluated (0.5 mg–5 mg) administered as a single bolus at least at 24, 48, or 72 hrs post surgery, or administered in multiple separate injections.

Osteochondral and chondral healing is evaluated grossly and histologically using routine protocols, including radiographs to evaluate healing. At twelve weeks post-operative each animal is sacrificed by an intravenous barbiturate overdose. Both right and left distal femurs are harvested en bloc and kept in cool saline until gross grading and microphotography are completed. The specimens are placed in 4% paraformaldehyde fixative, labeled with all necessary identifications, and stored at 4° C. until evaluated.

For histologic evaluation, the individual specimens are fixed by immersion in 4% paraformaldehyde solution and evaluated using standard procedures. In addition, using routine procedures, tissue typing analysis is performed in order to characterize the collagen type and percent tissue composition. Non-decalcified sections, one from each specimen, stained with Safranin-O and Fast Green stains (to indicate glycosaminoglycan content in the matrix), also can be used.

Osteochondral and/or condral defects treated with systemically administered osteogenic protein are anticipated to demonstrate bone and/or cartilage regeneration as the case may be, including appropriate chondrocyte and cartilage phenotype, including functional reparative articular cartilage formation, as compared with defects treated with the standard osteogenic device.

What is claimed is:

1. A method for determining the morphogenic ability of a candidate morphogenic protein to induce new tissue formation at a local defect site at least 6 hours after tissue damage, comprising the steps of:

(a) creating a local defect site accessible to progenitor cells, (b) administering at least 6 hours after creating the local defect site, said candidate morphogenic protein systemically to said mammal at a site distal from the local defect site, and (c) measuring the amount of new tissue formation at said defect site, wherein said local defect site is in renal, skeletal, lung, cardiac, liver, pancreas, uterine, ovarian, gastrointestinal, colon, dermal, osteochondral, chondral, or thyroid tissue, and wherein said morphogenic protein is selected from the group consisting of: OP1, OP2, OP3, BMP2, BMP3, BMP4, BMP5, BMP6, BMP9, BMP-10, BMP-11, BMP-12, BMP-15, BMP-3b, DPP, Vg1, Vgr-1, 60A protein, GDF-1, GDF-3, GDF-5, GDF-6, GDF-7, GDF-8, GDF-9, GDF-10, GDF-11, or amino acid sequence variants thereof; or wherein said candidate morphogenic protein comprises an amino acid sequence having at least 70% homology within the C-terminal 102 to 106 amino acids, including the conserved seven cysteine domain, of human OP1, and wherein the amount of new tissue formation at said defect site measured in step (c) that is greater than the amount of new tissue formation measured in the absence of administration of said candidate morphogenic protein indicates the ability of said candidate morphogenic protein to induce new tissue formation at a local defect site at least 6 hours after tissue damage.

2. A method for determining an optimal dosage of a candidate morphogenic protein for administering to a mammal to induce new tissue formation at a local defect site at least 6 hours after tissue damage, comprising the steps of:

(a) creating a local defect site accessible to progenitor cells, (b) administering at least 6 hours after creating the local defect site, said candidate morphogenic protein at a dosage to be tested systemically to said mammal at a site distal from the local defect site, and (c) measuring the amount of new tissue formation at said defect site, wherein said local defect site is in renal, skeletal, lung, cardiac, liver, pancreas, uterine, ovarian, gastrointestinal, colon, dermal, osteochondral, chondral, or thyroid tissue, and wherein said morphogenic protein is selected from the group consisting of: OP1, OP2, OP3, BMP2, BMP3, BMP4, BMP5, BMP6, BMP9, BMP-10, BMP-11, BMP-12, BMP-15, BMP-3b, DPP, Vg1, Vgr-1, 60A protein, GDF-1, GDF-3, GDF-5, GDF-6, GDF-7, GDF-8, GDF-9, GDF-10, GDF-11, or wherein said candidate morphogenic protein comprises an amino acid sequence having at least 70% homology within the C-terminal 102 to 106 amino acids, including the conserved seven cysteine domain, of human OP1, and wherein the dosage that induces the largest amount of new tissue formation at said defect site measured in step (c) indicates the optimal dosage of said candidate morphogenic protein to induce new tissue formation at a local defect site at least 6 hours after tissue damage.

3. The method of claim 1 or 2, wherein said defect site occurs in renal tissue.

4. The method of claim 1 or 2, wherein said mammal is aged.

5. The method of claim 1 or 2, wherein said mammal has a reduced capacity to induce callus formation.

6. The method of claim 1 or 2, wherein said mammal is afflicted with impaired blood flow to the skeletal extremities.

7. The method of claim 1 or 2, wherein said mammal has a reduced capacity to induce an endogenous morphogenic signal.

8. The method of claim 1 or 2, wherein said morphogenic protein or analog thereof is administered parenterally.

9. The method of claim 8, wherein said morphogenic protein or analog thereof is administered intravenously.

10. The method of claim 1 or 2, wherein said morphogenic protein or analog thereof is administered orally.

11. The method of claim 1, wherein said morphogenic protein or analog thereof is administered to said mammal at a time when mesenchymal progenitor cells are accessible to said local defect site.

12. The method of claim 1, wherein said morphogenic protein or analog thereof is administered at least 24 hours after the creation of said local defect site.

13. The method of claim 1, wherein said morphogenic protein or analog thereof is administered at least 72 hours after the creation of said local defect site.

14. The method of claim 1 or 2, wherein said morphogenic protein or analog thereof is administered to said mammal after the initiation of fibrosis at said local defect site.

15. The method of claim 1 or 2, wherein said morphogenic protein or analog thereof is administered in aqueous solution.

16. The method of claim 4, wherein said mammal is a steroidal drug user.

17. The method of claim 4, wherein said mammal is aged, obese, hypertensive, or afflicted with osteopenia or diabetes.

18. The method of claim 1 or 2, wherein said morphogenic protein is OP1.

19. The method of claim 1 or 2, wherein said morphogenic protein is mature OP1 solubilized in a saline solution.

20. The method of claim 1 or 2, wherein said morphogenic protein comprises an amino acid sequence defined by OPX (SEQ ID No. 3); Generic Sequence 6 (SEQ ID No. 4), Generic Sequence 7 (SEQ ID No. 5); Generic Sequence 8 (SEQ ID No. 6); or Generic Sequence 9 (SEQ ID No. 7).

21. The method of claim 1, wherein the ability of said candidate morphogenic protein or analog thereof to induce new tissue formation is measured by observation of actual new tissue formation by histological examination of the local defect site.

22. A method for determining the tissue regeneration activity of a candidate morphogenic protein at least 6 hours after tissue damage, comprising the steps of:

(a) creating a local defect site accessible to progenitor cells, (b) administering at least 6 hours after creating the local defect site, said candidate morphogenic protein systemically to said mammal at a site distal from the local defect site, and (c) measuring the extent of replacement tissue regeneration at the local defect site, induced by the administration of said candidate morphogenic protein, wherein said local defect site is in renal, skeletal, lung, cardiac, liver, pancreas, uterine, ovarian, gastrointestinal, colon, dermal, osteochondral, chondral, or thyroid tissue, and wherein said morphogenic protein is selected from the group consisting of: OP1, OP2, OP3, BMP2, BMP3, BMP4, BMP5, BMP6, BMP9, BMP-10, BMP-11, BMP-12, BMP-15, BMP-3b, DPP, Vg1, Vgr-1, 60A protein, GDF-1, GDF-3, GDF-5, GDF-6, GDF-7, GDF-8, GDF-9, GDF-10, GDF-11, or amino acid sequence variants thereof; or wherein said candidate morphogenic protein comprises an amino acid sequence having at least 70% homology within the C-terminal 102 to 106 amino acids, including the conserved seven cysteine domain, of human OP1, and wherein the amount of tissue regeneration at said defect site measured in step (c) that is greater than the amount measured in the absence of administration of said candidate morphogenic protein indicates the tissue regeneration activity of a candidate morphogenic protein at least 6 hours after tissue damage.

* * * * *

SEQUENCE LISTING

```
<160> NUMBER OF SEQ ID NOS:  9

<210> SEQ ID NO 1
<211> LENGTH: 1822
<212> TYPE: DNA
<213> ORGANISM: Homo sapiens
<220> FEATURE:
<221> NAME/KEY: CDS
<222> LOCATION: (49)..(1341)
<223> OTHER INFORMATION: "Morphogenic Protein OP-1"

<400> SEQUENCE: 1

ggtgcgggcc cggagcccgg agcccgggta gcgcgtagag ccggcgcg atg cac gtg       57
                                                     Met His Val
                                                       1

cgc tca ctg cga gct gcg gcg ccg cac agc ttc gtg gcg ctc tgg gca      105
Arg Ser Leu Arg Ala Ala Ala Pro His Ser Phe Val Ala Leu Trp Ala
      5                  10                  15

ccc ctg ttc ctg ctg cgc tcc gcc ctg gcc gac ttc agc ctg gac aac      153
Pro Leu Phe Leu Leu Arg Ser Ala Leu Ala Asp Phe Ser Leu Asp Asn
 20                  25                  30                  35

gag gtg cac tcg agc ttc atc cac cgg cgc ctc cgc agc cag gag cgg      201
Glu Val His Ser Ser Phe Ile His Arg Arg Leu Arg Ser Gln Glu Arg
                 40                  45                  50

cgg gag atg cag cgc gag atc ctc tcc att ttg ggc ttg ccc cac cgc      249
Arg Glu Met Gln Arg Glu Ile Leu Ser Ile Leu Gly Leu Pro His Arg
             55                  60                  65

ccg cgc ccg cac ctc cag ggc aag cac aac tcg gca ccc atg ttc atg      297
```

-continued

```
Pro Arg Pro His Leu Gln Gly Lys His Asn Ser Ala Pro Met Phe Met
         70                  75                  80

ctg gac ctg tac aac gcc atg gcg gtg gag gag ggc ggc ggg ccc ggc      345
Leu Asp Leu Tyr Asn Ala Met Ala Val Glu Glu Gly Gly Gly Pro Gly
     85                  90                  95

ggc cag ggc ttc tcc tac ccc tac aag gcc gtc ttc agt acc cag ggc      393
Gly Gln Gly Phe Ser Tyr Pro Tyr Lys Ala Val Phe Ser Thr Gln Gly
100                 105                 110                 115

ccc cct ctg gcc agc ctg caa gat agc cat ttc ctc acc gac gcc gac      441
Pro Pro Leu Ala Ser Leu Gln Asp Ser His Phe Leu Thr Asp Ala Asp
                120                 125                 130

atg gtc atg agc ttc gtc aac ctc gtg gaa cat gac aag gaa ttc ttc      489
Met Val Met Ser Phe Val Asn Leu Val Glu His Asp Lys Glu Phe Phe
            135                 140                 145

cac cca cgc tac cac cat cga gag ttc cgg ttt gat ctt tcc aag atc      537
His Pro Arg Tyr His His Arg Glu Phe Arg Phe Asp Leu Ser Lys Ile
        150                 155                 160

cca gaa ggg gaa gct gtc acg gca gcc gaa ttc cgg atc tac aag gac      585
Pro Glu Gly Glu Ala Val Thr Ala Ala Glu Phe Arg Ile Tyr Lys Asp
    165                 170                 175

tac atc cgg gaa cgc ttc gac aat gag acg ttc cgg atc agc gtt tat      633
Tyr Ile Arg Glu Arg Phe Asp Asn Glu Thr Phe Arg Ile Ser Val Tyr
180                 185                 190                 195

cag gtg ctc cag gag cac ttg ggc agg gaa tcg gat ctc ttc ctg ctc      681
Gln Val Leu Gln Glu His Leu Gly Arg Glu Ser Asp Leu Phe Leu Leu
                200                 205                 210

gac agc cgt acc ctc tgg gcc tcg gag gag ggc tgg ctg gtg ttt gac      729
Asp Ser Arg Thr Leu Trp Ala Ser Glu Glu Gly Trp Leu Val Phe Asp
            215                 220                 225

atc aca gcc acc agc aac cac tgg gtg gtc aat ccg cgg cac aac ctg      777
Ile Thr Ala Thr Ser Asn His Trp Val Val Asn Pro Arg His Asn Leu
        230                 235                 240

ggc ctg cag ctc tcg gtg gag acg ctg gat ggg cag agc atc aac ccc      825
Gly Leu Gln Leu Ser Val Glu Thr Leu Asp Gly Gln Ser Ile Asn Pro
    245                 250                 255

aag ttg gcg ggc ctg att ggg cgg cac ggg ccc cag aac aag cag ccc      873
Lys Leu Ala Gly Leu Ile Gly Arg His Gly Pro Gln Asn Lys Gln Pro
260                 265                 270                 275

ttc atg gtg gct ttc ttc aag gcc acg gag gtc cac ttc cgc agc atc      921
Phe Met Val Ala Phe Phe Lys Ala Thr Glu Val His Phe Arg Ser Ile
                280                 285                 290

cgg tcc acg ggg agc aaa cag cgc agc cag aac cgc tcc aag acg ccc      969
Arg Ser Thr Gly Ser Lys Gln Arg Ser Gln Asn Arg Ser Lys Thr Pro
            295                 300                 305

aag aac cag gaa gcc ctg cgg atg gcc aac gtg gca gag aac agc agc     1017
Lys Asn Gln Glu Ala Leu Arg Met Ala Asn Val Ala Glu Asn Ser Ser
        310                 315                 320

agc gac cag agg cag gcc tgt aag aag cac gag ctg tat gtc agc ttc     1065
Ser Asp Gln Arg Gln Ala Cys Lys Lys His Glu Leu Tyr Val Ser Phe
    325                 330                 335

cga gac ctg ggc tgg cag gac tgg atc atc gcg cct gaa ggc tac gcc     1113
Arg Asp Leu Gly Trp Gln Asp Trp Ile Ile Ala Pro Glu Gly Tyr Ala
340                 345                 350                 355

gcc tac tac tgt gag ggg gag tgt gcc ttc cct ctg aac tcc tac atg     1161
Ala Tyr Tyr Cys Glu Gly Glu Cys Ala Phe Pro Leu Asn Ser Tyr Met
                360                 365                 370

aac gcc acc aac cac gcc atc gtg cag acg ctg gtc cac ttc atc aac     1209
Asn Ala Thr Asn His Ala Ile Val Gln Thr Leu Val His Phe Ile Asn
            375                 380                 385
```

-continued

```
ccg gaa acg gtg ccc aag ccc tgc tgt gcg ccc acg cag ctc aat gcc      1257
Pro Glu Thr Val Pro Lys Pro Cys Cys Ala Pro Thr Gln Leu Asn Ala
        390                 395                 400

atc tcc gtc ctc tac ttc gat gac agc tcc aac gtc atc ctg aag aaa      1305
Ile Ser Val Leu Tyr Phe Asp Asp Ser Ser Asn Val Ile Leu Lys Lys
    405                 410                 415

tac aga aac atg gtg gtc cgg gcc tgt ggc tgc cac tagctcctcc          1351
Tyr Arg Asn Met Val Val Arg Ala Cys Gly Cys His
420                 425                 430

gagaattcag accctttggg gccaagtttt tctggatcct ccattgctcg ccttggccag   1411

gaaccagcag accaactgcc ttttgtgaga ccttcccctc cctatcccca actttaaagg   1471

tgtgagagta ttaggaaaca tgagcagcat atggcttttg atcagttttt cagtggcagc   1531

atccaatgaa caagatccta caagctgtgc aggcaaaacc tagcaggaaa aaaaaacaac   1591

gcataaagaa aaatggccgg gccaggtcat tggctgggaa gtctcagcca tgcacggact   1651

cgtttccaga ggtaattatg agcgcctacc agccaggcca cccagccgtg ggaggaaggg   1711

ggcgtggcaa ggggtgggca cattggtgtc tgtgcgaaag gaaaattgac ccggaagttc   1771

ctgtaataaa tgtcacaata aaacgaatga atgaaaaaaa aaaaaaaaaa a            1822


<210> SEQ ID NO 2
<211> LENGTH: 431
<212> TYPE: PRT
<213> ORGANISM: Homo sapiens

<400> SEQUENCE: 2

Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
     50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
```

-continued

```
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430


<210> SEQ ID NO 3
<211> LENGTH: 102
<212> TYPE: PRT
<213> ORGANISM: Artificial Sequence
<220> FEATURE:
<223> OTHER INFORMATION: Description of Artificial Sequence:  OPX
<221> NAME/KEY: VARIANT
<222> LOCATION: (1)..(102)
<223> OTHER INFORMATION: wherein each Xaa is independently selected from
      a group of one or more specified amino acids as defined in the
      specification

<400> SEQUENCE: 3

Cys Xaa Xaa His Glu Leu Tyr Val Ser Phe Xaa Asp Leu Gly Trp Xaa
  1               5                  10                  15

Asp Trp Xaa Ile Ala Pro Xaa Gly Tyr Xaa Ala Tyr Tyr Cys Glu Gly
             20                  25                  30

Glu Cys Xaa Phe Pro Leu Xaa Ser Xaa Met Asn Ala Thr Asn His Ala
         35                  40                  45

Ile Xaa Gln Xaa Leu Val His Xaa Xaa Xaa Pro Xaa Xaa Val Pro Lys
     50                  55                  60

Xaa Cys Cys Ala Pro Thr Xaa Leu Xaa Ala Xaa Ser Val Leu Tyr Xaa
 65                  70                  75                  80

Asp Xaa Ser Xaa Asn Val Ile Leu Xaa Lys Xaa Arg Asn Met Val Val
                 85                  90                  95

Xaa Ala Cys Gly Cys His
            100


<210> SEQ ID NO 4
<211> LENGTH: 97
<212> TYPE: PRT
<213> ORGANISM: Artificial Sequence
```

-continued

```
<220> FEATURE:
<223> OTHER INFORMATION: Description of Artificial Sequence: Generic
      Sequence 7
<221> NAME/KEY: VARIANT
<222> LOCATION: (1)..(97)
<223> OTHER INFORMATION: wherein each Xaa is independently selected from
      a group of one or more specified amino acids defined in the
      specification

<400> SEQUENCE: 4

Leu Xaa Xaa Xaa Phe Xaa Xaa Xaa Gly Trp Xaa Xaa Trp Xaa Xaa Xaa
  1               5                  10                  15

Pro Xaa Xaa Xaa Xaa Ala Xaa Tyr Cys Xaa Gly Xaa Cys Xaa Xaa Pro
             20                  25                  30

Xaa Xaa Xaa Xaa Xaa Xaa Xaa Xaa Asn His Ala Xaa Xaa Xaa Xaa Xaa
         35                  40                  45

Xaa Xaa Xaa Xaa Xaa Xaa Xaa Xaa Xaa Xaa Xaa Xaa Cys Cys Xaa Pro
     50                  55                  60

Xaa Xaa Xaa Xaa Xaa Xaa Xaa Xaa Leu Xaa Xaa Xaa Xaa Xaa Xaa Xaa
 65                  70                  75                  80

Val Xaa Leu Xaa Xaa Xaa Xaa Xaa Met Xaa Val Xaa Xaa Cys Xaa Cys
                 85                  90                  95

Xaa


<210> SEQ ID NO 5
<211> LENGTH: 102
<212> TYPE: PRT
<213> ORGANISM: Artificial Sequence
<220> FEATURE:
<223> OTHER INFORMATION: Description of Artificial Sequence:  Generic
      Sequence 8
<221> NAME/KEY: VARIANT
<222> LOCATION: ()..)
<223> OTHER INFORMATION: wherein each Xaa is independently selected from
      a group of one or more specified amino acids defined in the
      specification

<400> SEQUENCE: 5

Cys Xaa Xaa Xaa Xaa Leu Xaa Xaa Xaa Phe Xaa Xaa Xaa Gly Trp Xaa
  1               5                  10                  15

Xaa Xaa Xaa Xaa Xaa Pro Xaa Xaa Xaa Xaa Ala Xaa Tyr Cys Xaa Gly
             20                  25                  30

Xaa Cys Xaa Xaa Pro Xaa Xaa Xaa Xaa Xaa Xaa Xaa Xaa Asn His Ala
         35                  40                  45

Xaa Xaa Xaa Xaa Xaa Xaa Xaa Xaa Xaa Xaa Xaa Xaa Xaa Xaa Xaa Xaa
     50                  55                  60

Xaa Cys Cys Xaa Pro Xaa Xaa Xaa Xaa Xaa Xaa Xaa Xaa Leu Xaa Xaa
 65                  70                  75                  80

Xaa Xaa Xaa Xaa Xaa Val Xaa Leu Xaa Xaa Xaa Xaa Xaa Met Xaa Val
                 85                  90                  95

Xaa Xaa Cys Xaa Cys Xaa
            100


<210> SEQ ID NO 6
<211> LENGTH: 97
<212> TYPE: PRT
<213> ORGANISM: Artificial Sequence
<220> FEATURE:
<223> OTHER INFORMATION: Description of Artificial Sequence: Generic
      Sequence 9
<221> NAME/KEY: VARIANT
<222> LOCATION: ()..)
<223> OTHER INFORMATION: wherein each Xaa is independently selected from
```

-continued a group of one or more specified amino acids as defined in the specification

<400> SEQUENCE: 6

Xaa Xaa Xaa Xaa Xaa Xaa Xaa Xaa Xaa Xaa Xaa Xaa Xaa Xaa Xaa Xaa
1 5 10 15

Pro Xaa Xaa Xaa Xaa Xaa Xaa Xaa Cys Xaa Gly Xaa Cys Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Xaa Xaa Xaa Xaa Xaa Xaa Xaa Xaa Xaa Xaa Xaa Cys Xaa Pro
50 55 60

Xaa Xaa Xaa Xaa Xaa Xaa Xaa Xaa Leu Xaa Xaa Xaa Xaa Xaa Xaa Xaa
65 70 75 80

Xaa Xaa Xaa Xaa Xaa Xaa Xaa Xaa Xaa Xaa Xaa Xaa Xaa Cys Xaa Cys
85 90 95

Xaa

<210> SEQ ID NO 7
<211> LENGTH: 102
<212> TYPE: PRT
<213> ORGANISM: Artificial Sequence
<220> FEATURE:
<223> OTHER INFORMATION: Description of Artificial Sequence: Generic Sequence 10
<221> NAME/KEY: VARIANT
<222> LOCATION: ()..)
<223> OTHER INFORMATION: wherein each Xaa is independently selected from a group of one or more specified amino acids as defined in the specification

<400> SEQUENCE: 7

Cys Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Pro Xaa Xaa Xaa Xaa Xaa Xaa Xaa Cys Xaa Gly
20 25 30

Xaa Cys Xaa Xaa Xaa Xaa Xaa Xaa Xaa Xaa Xaa Xaa Xaa Xaa Xaa Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Cys Xaa Pro Xaa Xaa Xaa Xaa Xaa Xaa Xaa Xaa Leu Xaa Xaa
65 70 75 80

Xaa Xaa Xaa Xaa Xaa Xaa Xaa Xaa Xaa Xaa Xaa Xaa Xaa Xaa Xaa Xaa
85 90 95

Xaa Xaa Cys Xaa Cys Xaa
100

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Peptide
<221> NAME/KEY: VARIANT
<222> LOCATION: (1)..(5)
<223> OTHER INFORMATION: wherein each Xaa is independently selected from a group of one or more specified amino acids as defined in the specification

<400> SEQUENCE: 8

Cys Xaa Xaa Xaa Xaa
1 5

-continued

```
<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:  Peptide
<221> NAME/KEY: VARIANT
<222> LOCATION: (1)..(5)
<223> OTHER INFORMATION: wherein each Xaa is independently selected from
      a group of one or more specified amino acids as defined in the
      specification

<400> SEQUENCE: 9

Cys Xaa Xaa Xaa Xaa
  1             5
```